(12) United States Patent
Petisce et al.

(10) Patent No.: US 10,300,507 B2
(45) Date of Patent: May 28, 2019

(54) CELLULOSIC-BASED RESISTANCE DOMAIN FOR AN ANALYTE SENSOR

(71) Applicant: DexCom, Inc., San Diego, CA (US)

(72) Inventors: James R. Petisce, Westford, MA (US); Kum Ming Woo, San Diego, CA (US); Victor Ha, Saint Louis, MO (US); Melissa A. Nicholas, Monterey, CA (US)

(73) Assignee: DexCom, Inc., San Diego, CA (US)

( * ) Notice: Subject to any disclaimer, the term of this patent is extended or adjusted under 35 U.S.C. 154(b) by 439 days.

(21) Appl. No.: 14/181,434

(22) Filed: Feb. 14, 2014

(65) Prior Publication Data

US 2014/0161969 A1 Jun. 12, 2014

Related U.S. Application Data

(62) Division of application No. 11/413,238, filed on Apr. 28, 2006, now Pat. No. 8,744,546.
(Continued)

(51) Int. Cl.
*A61B 5/1473* (2006.01)
*A61B 5/145* (2006.01)
(Continued)

(52) U.S. Cl.
CPC .......... *B05D 1/005* (2013.01); *A61B 5/1473* (2013.01); *A61B 5/14532* (2013.01); *A61B 5/14542* (2013.01); *A61B 5/14546* (2013.01); *A61B 5/14865* (2013.01); *A61B 5/6848* (2013.01); *B05D 1/02* (2013.01); *C12Q 1/002* (2013.01); *C12Q 1/003* (2013.01); *G01N 33/54393* (2013.01); *G01N 33/66* (2013.01);
(Continued)

(58) Field of Classification Search
CPC ............ A61B 5/14532; A61B 5/14542; A61B 5/14546; A61B 5/1473; A61B 5/14865; A61B 5/6848; A61B 5/076; A61B 5/145; A61B 5/14503; C12Q 1/002; C12Q 1/003; G01N 33/54393; G01N 33/66; B05D 1/18; B05D 1/005; B05D 1/02
USPC ......................................... 600/309, 345–366
See application file for complete search history.

(56) References Cited

U.S. PATENT DOCUMENTS 2,830,020 A 4/1958 Chnstmann et al.
3,220,960 A 11/1965 Lim et al.
(Continued)

FOREIGN PATENT DOCUMENTS

EP 0 098 592 1/1984
EP 0 107 634 5/1984
(Continued)

OTHER PUBLICATIONS

Almanza-Workman et al, Characterization of highly hydrophobic coatings deposited onto preoxidized silicon from water dispersible organosilanes, 2003, Thin Solid Films, 423: 77-87.*
(Continued)

*Primary Examiner* — Navin Natnithithadha
(74) *Attorney, Agent, or Firm* — Knobbe Martens Olson & Bear, LLP

(57) ABSTRACT

The present invention relates generally to devices for measuring an analyte in a host. More particularly, the present invention relates to devices for measurement of glucose in a host that incorporate a cellulosic-based resistance domain.

14 Claims, 4 Drawing Sheets

Related U.S. Application Data

(60) Provisional application No. 60/678,373, filed on May 5, 2005.

(51) Int. Cl.
    *B05D 1/02*         (2006.01)
    *B05D 1/00*         (2006.01)
    *A61B 5/1486*     (2006.01)
    *A61B 5/00*         (2006.01)
    *C12Q 1/00*         (2006.01)
    *G01N 33/543*     (2006.01)
    *G01N 33/66*      (2006.01)
    *A61B 5/07*         (2006.01)

(52) U.S. Cl.
CPC .............. *A61B 5/076* (2013.01); *A61B 5/145* (2013.01); *A61B 5/14503* (2013.01)

(56) References Cited

U.S. PATENT DOCUMENTS

| | | |
|---|---|---|
| 3,562,352 A | 2/1971 | Nyilas |
| 3,607,329 A | 9/1971 | Manjikian |
| 3,746,588 A | 7/1973 | Brown, Jr. |
| 3,898,984 A | 8/1975 | Mandel et al. |
| 3,943,918 A | 3/1976 | Lewis |
| 3,964,974 A | 6/1976 | Banauch et al. |
| 3,979,274 A | 9/1976 | Newman |
| 4,003,621 A | 1/1977 | Lamp |
| 4,040,908 A | 8/1977 | Clark, Jr. |
| 4,073,713 A | 2/1978 | Newman |
| 4,136,250 A | 1/1979 | Mueller et al. |
| 4,172,770 A | 10/1979 | Semersky et al. |
| 4,240,889 A | 12/1980 | Yoda et al. |
| 4,253,469 A | 3/1981 | Aslan |
| 4,256,561 A | 3/1981 | Schindler et al. |
| 4,260,725 A | 4/1981 | Keogh et al. |
| 4,267,145 A | 5/1981 | Wysong |
| 4,292,423 A | 9/1981 | Kaufmann et al. |
| 4,340,457 A | 7/1982 | Kater |
| 4,353,888 A | 10/1982 | Sefton |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,418,148 A | 11/1983 | Oberhardt |
| 4,431,507 A | 2/1984 | Nankai et al. |
| 4,436,094 A | 3/1984 | Cerami |
| 4,442,841 A | 4/1984 | Uehara et al. |
| 4,454,295 A | 6/1984 | Wittmann et al. |
| 4,482,666 A | 11/1984 | Reeves |
| 4,484,987 A | 11/1984 | Gough |
| 4,493,714 A | 1/1985 | Ueda et al. |
| 4,494,950 A | 1/1985 | Fischell |
| 4,527,999 A | 7/1985 | Lee |
| 4,545,382 A | 10/1985 | Higgins et al. |
| 4,554,927 A | 11/1985 | Fussell |
| 4,602,922 A | 7/1986 | Cabasso et al. |
| 4,619,793 A | 10/1986 | Lee |
| 4,632,968 A | 12/1986 | Yokota et al. |
| 4,644,046 A | 2/1987 | Yamada |
| 4,647,643 A | 3/1987 | Zdrabala et al. |
| 4,650,547 A | 3/1987 | Gough |
| 4,671,288 A | 6/1987 | Gough |
| 4,672,970 A | 6/1987 | Uchida et al. |
| 4,675,346 A | 6/1987 | Lin et al. |
| 4,680,268 A | 7/1987 | Clark, Jr. |
| 4,684,538 A | 8/1987 | Klemarczyk |
| 4,684,558 A | 8/1987 | Keusch et al. |
| 4,685,463 A | 8/1987 | Williams |
| 4,686,137 A | 8/1987 | Ward, Jr. et al. |
| 4,689,149 A | 8/1987 | Kanno et al. |
| 4,689,309 A | 8/1987 | Jones |
| 4,703,756 A | 11/1987 | Gough et al. |
| 4,711,245 A | 12/1987 | Higgins |
| 4,721,677 A | 1/1988 | Clark, Jr. |
| 4,726,381 A | 2/1988 | Jones |
| 4,731,726 A | 3/1988 | Allen |
| 4,739,380 A | 4/1988 | Lauks et al. |
| 4,757,022 A | 7/1988 | Shults et al. |
| 4,759,828 A | 7/1988 | Young |
| 4,763,658 A | 8/1988 | Jones |
| 4,781,733 A | 11/1988 | Babcock et al. |
| 4,786,657 A | 11/1988 | Hammar et al. |
| 4,787,398 A | 11/1988 | Garcia et al. |
| 4,793,555 A | 12/1988 | Lee et al. |
| 4,795,542 A | 1/1989 | Ross et al. |
| 4,805,625 A | 2/1989 | Wyler |
| 4,810,470 A | 3/1989 | Burkhardt et al. |
| 4,813,424 A | 3/1989 | Wilkins |
| 4,822,336 A | 4/1989 | DiTraglia |
| 4,832,034 A | 5/1989 | Pizziconi |
| 4,852,573 A | 8/1989 | Kennedy |
| 4,861,830 A | 8/1989 | Ward, Jr. |
| 4,871,440 A | 10/1989 | Nagata et al. |
| 4,880,883 A | 11/1989 | Grasel et al. |
| 4,886,740 A | 12/1989 | Vadgama |
| 4,890,620 A | 1/1990 | Gough |
| 4,908,208 A | 3/1990 | Lee et al. |
| 4,909,908 A | 3/1990 | Ross et al. |
| 4,919,141 A | 4/1990 | Zier et al. |
| 4,935,345 A | 6/1990 | Guilbeauet et al. |
| 4,938,860 A | 7/1990 | Wogoman |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,970,145 A | 11/1990 | Bennetto et al. |
| 4,973,320 A | 11/1990 | Brenner et al. |
| 4,988,341 A | 1/1991 | Columbus et al. |
| 4,989,607 A | 2/1991 | Keusch et al. |
| 4,994,167 A | 2/1991 | Shults et al. |
| 5,002,590 A | 3/1991 | Friesen et al. |
| 5,010,141 A | 4/1991 | Mueller |
| 5,034,461 A | 7/1991 | Lai et al. |
| 5,035,711 A | 7/1991 | Aoki et al. |
| 5,045,601 A | 9/1991 | Capelli et al. |
| 5,050,612 A | 9/1991 | Matsumura |
| 5,059,654 A | 10/1991 | Hou et al. |
| 5,063,081 A | 11/1991 | Cozzette et al. |
| 5,070,169 A | 12/1991 | Robertson et al. |
| 5,071,452 A | 12/1991 | Avrillon et al. |
| 5,082,550 A | 1/1992 | Rishpon et al. |
| 5,094,876 A | 3/1992 | Goldberg et al. |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint, Jr. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,242,835 A | 9/1993 | Jensen |
| 5,249,576 A | 10/1993 | Goldberger et al. |
| 5,250,439 A | 10/1993 | Musho et al. |
| 5,262,305 A | 11/1993 | Heller et al. |
| 5,264,104 A | 11/1993 | Gregg et al. |
| 5,264,105 A * | 11/1993 | Gregg .................. C12Q 1/002 204/403.09 |
| 5,269,891 A | 12/1993 | Colin |

(56) References Cited

U.S. PATENT DOCUMENTS

| | | |
|---|---|---|
| 5,284,140 A | 2/1994 | Allen et al. |
| 5,286,364 A | 2/1994 | Yacynych et al. |
| 5,296,144 A | 3/1994 | Sternina et al. |
| 5,299,571 A | 4/1994 | Mastrototaro |
| 5,302,440 A | 4/1994 | Davis |
| 5,304,468 A | 4/1994 | Phillips et al. |
| 5,310,469 A | 5/1994 | Cunningham et al. |
| 5,314,471 A | 5/1994 | Brauker et al. |
| 5,316,008 A | 5/1994 | Suga et al. |
| 5,322,063 A * | 6/1994 | Allen .............. C12Q 1/002 |
| | | 204/403.11 |
| 5,324,322 A | 6/1994 | Grill et al. |
| 5,331,555 A | 7/1994 | Hashimoto et al. |
| 5,334,681 A | 8/1994 | Mueller et al. |
| 5,336,102 A | 8/1994 | Cairns et al. |
| 5,342,693 A | 8/1994 | Winters et al. |
| 5,344,454 A | 9/1994 | Clarke et al. |
| 5,352,348 A | 10/1994 | Young et al. |
| 5,356,786 A | 10/1994 | Heller et al. |
| 5,372,133 A | 12/1994 | Hogen Esch |
| 5,376,400 A | 12/1994 | Goldberg et al. |
| 5,380,536 A | 1/1995 | Hubbell et al. |
| 5,384,028 A | 1/1995 | Ito |
| 5,387,327 A | 2/1995 | Khan |
| 5,387,329 A | 2/1995 | Foos et al. |
| 5,390,671 A | 2/1995 | Lord et al. |
| 5,391,250 A | 2/1995 | Cheney, II et al. |
| 5,397,451 A | 3/1995 | Senda et al. |
| 5,397,848 A | 3/1995 | Yang et al. |
| 5,411,647 A | 5/1995 | Johnson et al. |
| 5,411,866 A | 5/1995 | Luong |
| 5,426,158 A | 6/1995 | Mueller et al. |
| 5,428,123 A | 6/1995 | Ward et al. |
| 5,429,735 A | 7/1995 | Johnson et al. |
| 5,438,984 A | 8/1995 | Schoendorfer |
| 5,453,248 A | 9/1995 | Olstein |
| 5,453,278 A | 9/1995 | Chan et al. |
| 5,462,051 A | 10/1995 | Oka et al. |
| 5,466,575 A | 11/1995 | Cozzette et al. |
| 5,469,846 A | 11/1995 | Khan |
| 5,476,094 A | 12/1995 | Allen et al. |
| 5,482,473 A | 1/1996 | Lord et al. |
| 5,494,562 A | 2/1996 | Maley et al. |
| 5,497,772 A | 3/1996 | Schulman et al. |
| 5,507,288 A | 4/1996 | Bocker et al. |
| 5,513,636 A | 5/1996 | Palti |
| 5,518,601 A | 5/1996 | Foos et al. |
| 5,521,273 A | 5/1996 | Yilgor et al. |
| 5,531,878 A | 7/1996 | Vadgama et al. |
| 5,541,305 A | 7/1996 | Yokota et al. |
| 5,545,223 A | 8/1996 | Neuenfeldt et al. |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,575,930 A | 11/1996 | Tietje-Girault et al. |
| 5,578,463 A | 11/1996 | Berka et al. |
| 5,582,184 A | 12/1996 | Erickson et al. |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,589,563 A | 12/1996 | Ward et al. |
| 5,593,440 A | 1/1997 | Brauker et al. |
| 5,593,852 A | 1/1997 | Heller et al. |
| 5,607,565 A | 3/1997 | Azarnia et al. |
| 5,611,900 A | 3/1997 | Worden |
| 5,624,537 A | 4/1997 | Turner et al. |
| 5,640,954 A | 6/1997 | Pfeiffer |
| 5,653,756 A | 8/1997 | Clarke et al. |
| 5,665,222 A | 9/1997 | Heller et al. |
| 5,670,097 A | 9/1997 | Duan et al. |
| 5,683,562 A | 11/1997 | Schaffar et al. |
| 5,695,623 A | 12/1997 | Michel et al. |
| 5,697,976 A | 12/1997 | Chesterfield et al. |
| 5,700,559 A | 12/1997 | Sheu et al. |
| 5,703,359 A | 12/1997 | Wampler, III |
| 5,711,861 A | 1/1998 | Ward et al. |
| 5,713,888 A | 2/1998 | Neuenfeldt et al. |
| 5,733,336 A | 3/1998 | Neuenfeldt et al. |
| 5,741,330 A | 4/1998 | Brauker et al. |
| 5,743,262 A | 4/1998 | Lepper, Jr. et al. |
| 5,746,898 A | 5/1998 | Priedel |
| 5,756,632 A | 5/1998 | Ward et al. |
| 5,760,155 A | 6/1998 | Mowrer et al. |
| 5,766,839 A | 6/1998 | Johnson et al. |
| 5,773,270 A | 6/1998 | D'Orazio et al. |
| 5,773,286 A | 6/1998 | Dionne et al. |
| 5,776,324 A | 7/1998 | Usala |
| 5,777,060 A | 7/1998 | Van Antwerp |
| 5,786,439 A | 7/1998 | Van Antwerp et al. |
| 5,791,344 A | 8/1998 | Schulman et al. |
| 5,795,453 A | 8/1998 | Gilmartin |
| 5,795,774 A | 8/1998 | Matsumoto et al. |
| 5,800,420 A | 9/1998 | Gross |
| 5,804,048 A | 9/1998 | Wong et al. |
| 5,807,375 A | 9/1998 | Gross et al. |
| 5,807,636 A | 9/1998 | Sheu et al. |
| 5,820,570 A | 10/1998 | Erickson |
| 6,820,622 B1 | 10/1998 | Gross et al. |
| 5,833,603 A | 11/1998 | Kovacs et al. |
| 5,834,583 A | 11/1998 | Hancock et al. |
| 5,837,377 A | 11/1998 | Sheu et al. |
| 5,837,454 A | 11/1998 | Cozzette et al. |
| 5,837,661 A | 11/1998 | Evans et al. |
| 5,843,069 A | 12/1998 | Butler et al. |
| 5,851,229 A | 12/1998 | Lentz et al. |
| 5,858,747 A | 1/1999 | Schinstine et al. |
| 5,863,972 A | 1/1999 | Beckelmann et al. |
| 5,879,713 A | 3/1999 | Roth et al. |
| 5,882,494 A | 3/1999 | Van Antwerp |
| 5,885,566 A | 3/1999 | Goldberg |
| 5,897,955 A | 4/1999 | Drumheller |
| 5,910,554 A | 6/1999 | Kempe et al. |
| 5,914,026 A | 6/1999 | Blubaugh, Jr. |
| 5,914,182 A | 6/1999 | Drumheller |
| 5,931,814 A | 8/1999 | Alex et al. |
| 5,932,299 A | 8/1999 | Katoot |
| 5,945,498 A | 8/1999 | Hopken et al. |
| 5,947,127 A | 9/1999 | Tsugaya et al. |
| 5,954,643 A | 9/1999 | Van Antwerp et al. |
| 5,955,066 A | 9/1999 | Sako et al. |
| 5,957,854 A | 9/1999 | Besson et al. |
| 5,959,191 A | 9/1999 | Lewis et al. |
| 5,961,451 A | 10/1999 | Reber et al. |
| 5,964,993 A | 10/1999 | Blubaugh et al. |
| 5,965,125 A | 10/1999 | Mineau-Hanschke |
| 5,965,380 A | 10/1999 | Heller et al. |
| 5,969,076 A | 10/1999 | Lai et al. |
| 5,972,199 A | 10/1999 | Heller |
| 5,972,369 A | 10/1999 | Roorda et al. |
| 5,977,241 A | 11/1999 | Koloski et al. |
| 5,985,129 A | 11/1999 | Gough et al. |
| 6,001,067 A | 12/1999 | Shults et al. |
| 6,002,954 A | 12/1999 | Van Antwerp et al. |
| 6,007,845 A | 12/1999 | Domb |
| 6,011,984 A | 1/2000 | Van Antwerp et al. |
| 6,018,013 A | 1/2000 | Yoshida et al. |
| 6,018,033 A | 1/2000 | Chen et al. |
| 6,022,463 A | 2/2000 | Leader et al. |
| 6,030,827 A | 2/2000 | Davis et al. |
| 6,039,913 A | 3/2000 | Hirt et al. |
| 6,043,328 A | 3/2000 | Domschke et al. |
| 6,045,671 A | 4/2000 | Wu et al. |
| 6,051,389 A | 4/2000 | Ahl et al. |
| 6,059,946 A | 5/2000 | Yukawa et al. |
| 6,066,448 A | 5/2000 | Wohlstadter et al. |
| 6,740,059 B2 | 5/2000 | Hulings et al. |
| 6,071,406 A | 6/2000 | Tsou |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |

(56) References Cited

U.S. PATENT DOCUMENTS

| | | | |
|---|---|---|---|
| 6,091,975 A | 7/2000 | Daddona et al. | |
| 6,093,172 A | 7/2000 | Funderburk et al. | |
| 6,103,033 A | 8/2000 | Say et al. | |
| 6,107,083 A | 8/2000 | Collins et al. | |
| 6,119,028 A | 9/2000 | Schulman et al. | |
| 6,120,676 A | 9/2000 | Heller et al. | |
| 6,121,009 A | 9/2000 | Heller et al. | |
| 6,122,536 A | 9/2000 | Sun et al. | |
| 6,127,154 A | 10/2000 | Mosbach et al. | |
| 6,134,461 A | 10/2000 | Say et al. | |
| 6,162,611 A | 12/2000 | Heller et al. | |
| 6,175,752 B1 | 1/2001 | Say et al. | |
| 6,200,772 B1 | 3/2001 | Vadgama et al. | |
| 6,212,416 B1 | 4/2001 | Ward et al. | |
| 6,214,185 B1 | 4/2001 | Offenbacher et al. | |
| 6,233,471 B1 | 5/2001 | Berner et al. | |
| 6,241,863 B1 | 6/2001 | Monbouquette | |
| 6,248,067 B1 | 6/2001 | Causey, III et al. | |
| 6,254,586 B1 | 7/2001 | Mann et al. | |
| 6,256,522 B1 | 7/2001 | Schultz | |
| 6,259,937 B1 | 7/2001 | Schulman et al. | |
| 6,264,825 B1 | 7/2001 | Blackburn et al. | |
| 6,271,332 B1 | 8/2001 | Lohmann et al. | |
| 6,274,666 B1 | 8/2001 | Mosbach et al. | |
| 6,275,717 B1 | 8/2001 | Gross et al. | |
| 6,284,478 B1 | 9/2001 | Heller et al. | |
| 6,299,583 B1 | 10/2001 | Eggers et al. | |
| 6,303,670 B1 | 10/2001 | Fujino et al. | |
| 6,306,594 B1 | 10/2001 | Cozzette | |
| 6,312,706 B1 | 11/2001 | Lai et al. | |
| 6,329,161 B1 | 12/2001 | Heller et al. | |
| 6,329,488 B1 | 12/2001 | Terry et al. | |
| 6,330,464 B1 | 12/2001 | Colvin, Jr. et al. | |
| 6,343,225 B1 | 1/2002 | Clark, Jr. | |
| 6,358,557 B1 | 3/2002 | Wang et al. | |
| 6,368,658 B1 | 4/2002 | Schwarz et al. | |
| 6,379,883 B2 | 4/2002 | Davis et al. | |
| 6,387,379 B1 | 5/2002 | Goldberg et al. | |
| 6,395,325 B1 | 5/2002 | Hedge et al. | |
| 6,400,974 B1 | 6/2002 | Lesho | |
| 6,405,066 B1 | 6/2002 | Essenpreis et al. | |
| 6,407,195 B2 | 6/2002 | Sherman et al. | |
| 6,413,393 B1 | 7/2002 | Van Antwerp et al. | |
| 6,413,396 B1 | 7/2002 | Yang et al. | |
| 6,424,847 B1 | 7/2002 | Mastrototaro et al. | |
| 6,442,413 B1 | 8/2002 | Silver | |
| 6,461,496 B1 | 10/2002 | Feldman et al. | |
| 6,465,066 B1 | 10/2002 | Rule et al. | |
| 6,466,810 B1 | 10/2002 | Ward et al. | |
| 6,475,750 B1 | 11/2002 | Han et al. | |
| 6,484,046 B1 | 11/2002 | Say et al. | |
| 6,497,729 B1 | 12/2002 | Moussy et al. | |
| 6,512,939 B1 | 1/2003 | Colvin et al. | |
| 6,514,718 B2 | 2/2003 | Heller et al. | |
| 6,528,584 B2 | 3/2003 | Kennedy et al. | |
| 6,551,496 B1 | 4/2003 | Moles et al. | |
| 6,554,982 B1 | 4/2003 | Shin et al. | |
| 6,565,509 B1 | 5/2003 | Say et al. | |
| 6,579,498 B1 | 6/2003 | Eglise | |
| 6,579,690 B1 | 6/2003 | Bonnecaze et al. | |
| 6,596,294 B2 | 7/2003 | Lai et al. | |
| 6,613,379 B2 | 9/2003 | Ward et al. | |
| 6,618,934 B1 | 9/2003 | Feldman et al. | |
| 6,633,772 B2 | 10/2003 | Ford et al. | |
| 6,642,015 B2 | 11/2003 | Vachon et al. | |
| 6,654,625 B1 | 11/2003 | Say et al. | |
| 6,670,115 B1 | 12/2003 | Zhang | |
| 6,689,265 B2 | 2/2004 | Heller et al. | |
| 6,692,528 B2 | 2/2004 | Ward et al. | |
| 6,702,857 B2 | 3/2004 | Brauker et al. | |
| 6,702,972 B1 | 3/2004 | Markle | |
| 6,721,587 B2 | 4/2004 | Gough | |
| 6,741,877 B1 | 5/2004 | Shults et al. | |
| 6,784,274 B2 | 8/2004 | van Antwerp et al. | |
| 6,789,634 B1 | 9/2004 | Denton | |
| 6,793,789 B2 | 9/2004 | Choi et al. | |
| 6,801,041 B2 | 10/2004 | Karinka et al. | |
| 6,802,957 B2 | 10/2004 | Jung et al. | |
| 6,816,186 B2 | 11/2004 | Clarke, Jr. | |
| 6,858,218 B2 | 2/2005 | Lai et al. | |
| 6,862,465 B2 | 3/2005 | Shults et al. | |
| 6,867,262 B1 | 3/2005 | Angel et al. | |
| 6,881,551 B2 | 4/2005 | Heller et al. | |
| 6,895,263 B2 | 5/2005 | Shin et al. | |
| 6,895,265 B2 | 5/2005 | Silver | |
| 6,908,681 B2 | 6/2005 | Terry et al. | |
| 6,932,894 B2 | 8/2005 | Mao et al. | |
| 6,965,791 B1 | 11/2005 | Hitchcock et al. | |
| 6,969,451 B2 | 11/2005 | Shin et al. | |
| 6,973,706 B2 | 12/2005 | Say et al. | |
| 7,008,979 B2 | 3/2006 | Schottman et al. | |
| 7,014,948 B2 | 3/2006 | Lee et al. | |
| 7,033,322 B2 | 4/2006 | Silver | |
| 7,052,131 B2 | 5/2006 | McCabe et al. | |
| 7,108,778 B2 | 9/2006 | Simpson et al. | |
| 7,110,803 B2 | 9/2006 | Shults et al. | |
| 7,118,667 B2 | 10/2006 | Lee | |
| 7,120,483 B2 | 10/2006 | Russell et al. | |
| 7,136,689 B2 | 11/2006 | Shults et al. | |
| 7,153,265 B2 | 12/2006 | Vachon | |
| 7,157,528 B2 | 1/2007 | Ward | |
| 7,172,075 B1 | 2/2007 | Ji | |
| 7,192,450 B2 | 3/2007 | Brauker et al. | |
| 7,226,978 B2 | 6/2007 | Tapsak et al. | |
| 7,229,471 B2 | 6/2007 | Gale et al. | |
| 7,241,586 B2 | 7/2007 | Gulati | |
| 7,248,906 B2 | 7/2007 | Dirac et al. | |
| 7,279,174 B2 | 10/2007 | Pacetti et al. | |
| 7,299,052 B2 | 11/2007 | Feldman et al. | |
| 7,310,544 B2 | 12/2007 | Brister et al. | |
| 7,335,286 B2 | 2/2008 | Abel et al. | |
| 7,336,984 B2 | 2/2008 | Gough et al. | |
| 7,357,793 B2 | 4/2008 | Pacetti | |
| 7,366,566 B2 | 4/2008 | Brister et al. | |
| 7,379,765 B2 | 5/2008 | Petisce et al. | |
| 7,417,164 B2 | 8/2008 | Suri | |
| 7,423,074 B2 | 9/2008 | Lai et al. | |
| 7,470,488 B2 | 12/2008 | Lee et al. | |
| 7,613,491 B2 | 11/2009 | Boock et al. | |
| 7,651,596 B2 | 1/2010 | Petisce et al. | |
| 7,670,470 B2 | 3/2010 | Mao et al. | |
| 2002/0018843 A1 | 2/2002 | Van Antwerp et al. | |
| 2002/0022883 A1 | 2/2002 | Burg | |
| 2002/0042090 A1 | 4/2002 | Heller et al. | |
| 2002/0043471 A1 | 4/2002 | Ikeda et al. | |
| 2002/0055673 A1 | 5/2002 | Van Antwerp et al. | |
| 2002/0068860 A1 | 6/2002 | Clark, Jr. | |
| 2002/0123087 A1 | 9/2002 | Vachon et al. | |
| 2002/0128546 A1 | 9/2002 | Silver | |
| 2002/0151796 A1 | 10/2002 | Koutik | |
| 2002/0156355 A1 | 10/2002 | Gough | |
| 2002/0162792 A1 | 11/2002 | Zepf | |
| 2002/0182241 A1 | 12/2002 | Borenstein et al. | |
| 2002/0185384 A1 | 12/2002 | Leong et al. | |
| 2002/0193885 A1 | 12/2002 | Legeay et al. | |
| 2003/0009093 A1 | 1/2003 | Silver | |
| 2003/0023317 A1 | 1/2003 | Brauker et al. | |
| 2003/0031699 A1 | 2/2003 | Van Antwerp | |
| 2003/0032874 A1* | 2/2003 | Rhodes | A61B 5/14532 600/347 |
| 2003/0059631 A1 | 3/2003 | Al-Lamee | |
| 2003/0065254 A1 | 4/2003 | Schulman et al. | |
| 2003/0069383 A1 | 4/2003 | Van Antwerp et al. | |
| 2003/0070548 A1 | 4/2003 | Clausen | |
| 2003/0072741 A1 | 4/2003 | Berglund et al. | |
| 2003/0088166 A1 | 5/2003 | Say et al. | |
| 2003/0096424 A1 | 5/2003 | Mao et al. | |
| 2003/0099682 A1 | 5/2003 | Moussy et al. | |
| 2003/0100040 A1* | 5/2003 | Bonnecaze | A61B 5/0031 435/14 |
| 2003/0104273 A1 | 6/2003 | Lee et al. | |
| 2003/0125403 A1* | 7/2003 | Steine | B01D 67/0011 521/50 |
| 2003/0125498 A1 | 7/2003 | McCabe et al. | |

(56) References Cited

U.S. PATENT DOCUMENTS

| | | |
|---|---|---|
| 2003/0132227 A1 | 7/2003 | Geisler |
| 2003/0134100 A1 | 7/2003 | Mao et al. |
| 2003/0134347 A1 | 7/2003 | Heller et al. |
| 2003/0157409 A1 | 8/2003 | Huang et al. |
| 2003/0181794 A1 | 9/2003 | Rini et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0199878 A1 | 10/2003 | Pohjonen |
| 2003/0200040 A1 | 10/2003 | Trygg et al. |
| 2003/0203991 A1 | 10/2003 | Schottman et al. |
| 2003/0211050 A1 | 11/2003 | Majeti et al. |
| 2003/0217966 A1 | 11/2003 | Tapsak et al. |
| 2003/0225324 A1 | 12/2003 | Anderson et al. |
| 2003/0228631 A1 | 12/2003 | Ritts et al. |
| 2003/0235617 A1 | 12/2003 | Bartkowiak et al. |
| 2004/0006263 A1 | 1/2004 | Anderson et al. |
| 2004/0011671 A1 | 1/2004 | Shults et al. |
| 2004/0023317 A1 | 2/2004 | Motamedi et al. |
| 2004/0045879 A1 | 3/2004 | Shults et al. |
| 2004/0063167 A1 | 4/2004 | Kaastrup et al. |
| 2004/0074785 A1* | 4/2004 | Holker ............ A61B 5/1486 205/777.5 |
| 2004/0084306 A1 | 5/2004 | Shin et al. |
| 2004/0106741 A1 | 6/2004 | Kriesel et al. |
| 2004/0106857 A1 | 6/2004 | Gough |
| 2004/0111017 A1 | 6/2004 | Say et al. |
| 2004/0111144 A1 | 6/2004 | Lawin et al. |
| 2004/0120848 A1* | 6/2004 | Teodorczyk ........ A61L 2/0011 422/22 |
| 2004/0138543 A1 | 7/2004 | Russell et al. |
| 2004/0143173 A1 | 7/2004 | Reghabi et al. |
| 2004/0167801 A1 | 8/2004 | Say et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0213985 A1 | 10/2004 | Lee |
| 2004/0224001 A1 | 11/2004 | Pacetti et al. |
| 2004/0228902 A1 | 11/2004 | Benz |
| 2004/0234575 A1 | 11/2004 | Horres et al. |
| 2004/0248282 A1 | 12/2004 | Sobha et al. |
| 2004/0253365 A1 | 12/2004 | Warren et al. |
| 2004/0265940 A1 | 12/2004 | Slater et al. |
| 2005/0003399 A1 | 1/2005 | Blackburn et al. |
| 2005/0013842 A1 | 1/2005 | Qiu et al. |
| 2005/0031689 A1 | 2/2005 | Shults et al. |
| 2005/0033132 A1 | 2/2005 | Shults et al. |
| 2005/0054909 A1 | 3/2005 | Petisce et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |
| 2005/0044088 A1 | 5/2005 | Agus |
| 2005/0103625 A1 | 5/2005 | Rhodes et al. |
| 2005/0107677 A1 | 5/2005 | Ward et al. |
| 2005/0112169 A1 | 5/2005 | Brauker et al. |
| 2005/0112172 A1 | 5/2005 | Pacetti |
| 2005/0112358 A1 | 5/2005 | Potyrailo et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say |
| 2005/0124873 A1 | 6/2005 | Shults et al. |
| 2005/0139489 A1 | 6/2005 | Oliver et al. |
| 2005/0143635 A1 | 6/2005 | Kamath et al. |
| 2005/0154271 A1 | 7/2005 | Rasdal et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0184641 A1 | 8/2005 | Armitage et al. |
| 2005/0192557 A1 | 9/2005 | Brauker et al. |
| 2005/0196747 A1 | 9/2005 | Stiene |
| 2005/0197554 A1 | 9/2005 | Polcha |
| 2005/0209665 A1 | 9/2005 | Hunter et al. |
| 2005/0215871 A1 | 9/2005 | Feldman et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2005/0271546 A1 | 12/2005 | Gerber et al. |
| 2005/0274665 A1 | 12/2005 | Heilmann et al. |
| 2005/0282997 A1 | 12/2005 | Ward |
| 2006/0003398 A1 | 1/2006 | Heller et al. |
| 2006/0007391 A1 | 1/2006 | McCabe et al. |
| 2006/0008370 A1 | 1/2006 | Massaro et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047095 A1 | 3/2006 | Pacetti |
| 2006/0058868 A1 | 3/2006 | Gale et al. |
| 2006/0065527 A1 | 3/2006 | Samproni |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0086624 A1 | 4/2006 | Tapsak et al. |
| 2006/0134165 A1 | 6/2006 | Pacetti |
| 2006/0142524 A1 | 6/2006 | Lai et al. |
| 2006/0142525 A1 | 6/2006 | Lai et al. |
| 2006/0142526 A1 | 6/2006 | Lai et al. |
| 2006/0142651 A1 | 6/2006 | Brister et al. |
| 2006/0148985 A1 | 7/2006 | Karthauser |
| 2006/0155180 A1 | 7/2006 | Brister et al. |
| 2006/0159718 A1 | 7/2006 | Rathenow et al. |
| 2006/0171980 A1 | 8/2006 | Helmus et al. |
| 2006/0177379 A1 | 8/2006 | Asgari |
| 2006/0183178 A1 | 8/2006 | Gulati |
| 2006/0183871 A1 | 8/2006 | Ward et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269585 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2007/0003588 A1 | 1/2007 | Chinn et al. |
| 2007/0007133 A1 | 1/2007 | Mang et al. |
| 2007/0027385 A1 | 2/2007 | Brister et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |

(56) References Cited

U.S. PATENT DOCUMENTS

| | | |
|---|---|---|
| 2007/0042377 A1* | 2/2007 | Gao .................. B01D 69/141 435/6.11 |
| 2007/0045902 A1 | 3/2007 | Brauker et al. |
| 2007/0059196 A1 | 3/2007 | Brister et al. |
| 2007/0123963 A1 | 5/2007 | Krulevitch |
| 2007/0129524 A1 | 6/2007 | Sunkara |
| 2007/0135698 A1 | 6/2007 | Shah et al. |
| 2007/0142584 A1 | 6/2007 | Schorzman et al. |
| 2007/0155851 A1 | 7/2007 | Alii et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0197890 A1 | 8/2007 | Boock et al. |
| 2007/0200267 A1 | 8/2007 | Tsai |
| 2007/0202562 A1 | 8/2007 | Curry |
| 2007/0203568 A1 | 8/2007 | Gale et al. |
| 2007/0203573 A1 | 8/2007 | Rudakov et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0233013 A1 | 10/2007 | Schoenberg |
| 2007/0235331 A1 | 10/2007 | Simpson |
| 2007/0242215 A1 | 10/2007 | Schorzman et al. |
| 2007/0244379 A1 | 10/2007 | Boock et al. |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0001318 A1 | 1/2008 | Schorzman et al. |
| 2008/0021008 A1 | 1/2008 | Pacetti et al. |
| 2008/0027301 A1 | 1/2008 | Ward et al. |
| 2008/0031918 A1 | 2/2008 | Lawin et al. |
| 2008/0033269 A1 | 2/2008 | Zhang |
| 2008/0034972 A1 | 2/2008 | Gough et al. |
| 2008/0038307 A1 | 2/2008 | Hoffmann |
| 2008/0045824 A1 | 2/2008 | Tapsak et al. |
| 2008/0071027 A1 | 3/2008 | Pacetti |
| 2008/0076897 A1 | 3/2008 | Kunzler et al. |
| 2008/0081184 A1 | 4/2008 | Kubo et al. |
| 2008/0113207 A1 | 5/2008 | Pacetti et al. |
| 2008/0138497 A1 | 6/2008 | Pacetti et al. |
| 2008/0138498 A1 | 6/2008 | Pacetti et al. |
| 2008/0143014 A1 | 6/2008 | Tang |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0210557 A1 | 9/2008 | Heller et al. |
| 2008/0213460 A1 | 9/2008 | Benter et al. |
| 2008/0305009 A1 | 12/2008 | Gamsey et al. |
| 2008/0305506 A1 | 12/2008 | Suri |
| 2008/0312397 A1 | 12/2008 | Lai et al. |
| 2009/0004243 A1 | 1/2009 | Pacetti et al. |
| 2009/0012205 A1 | 1/2009 | Nakada et al. |
| 2009/0018418 A1 | 1/2009 | Markle |
| 2009/0018426 A1 | 1/2009 | Markle et al. |
| 2009/0030294 A1 | 1/2009 | Petisce et al. |
| 2009/0045055 A1 | 2/2009 | Rhodes et al. |
| 2009/0061528 A1 | 3/2009 | Suri |
| 2009/0081803 A1 | 3/2009 | Gamsey et al. |
| 2009/0177143 A1 | 7/2009 | Markle et al. |
| 2009/0247855 A1 | 10/2009 | Boock et al. |
| 2009/0247856 A1 | 10/2009 | Boock et al. |
| 2009/0264719 A1 | 10/2009 | Markle et al. |
| 2009/0287073 A1 | 11/2009 | Boock et al. |
| 2010/0076283 A1 | 3/2010 | Simpson et al. |
| 2010/0096259 A1 | 4/2010 | Zhang et al. |
| 2010/0119693 A1 | 5/2010 | Tapsak et al. |

FOREIGN PATENT DOCUMENTS

| | | |
|---|---|---|
| EP | 0 127 958 | 12/1984 |
| EP | 0 291 130 | 11/1988 |
| EP | 0 313 951 | 5/1989 |
| EP | 0 320 109 | 6/1989 |
| EP | 0 353 328 | 2/1990 |
| EP | 0 362 145 | 4/1990 |
| EP | 0 390 390 | 10/1990 |
| EP | 0 396 788 | 11/1990 |
| EP | 0 535 898 | 4/1993 |
| EP | 0 563 795 | 10/1993 |
| EP | 0 286 118 | 1/1995 |
| EP | 0 747 069 | 12/1996 |
| EP | 0 817 809 | 1/1998 |
| EP | 0 862 648 | 9/1998 |
| EP | 0 789 540 | 9/2001 |
| EP | 1 153 571 | 11/2001 |
| GB | 2149918 | 6/1985 |
| GB | 2209836 | 5/1989 |
| JP | 59209610 | 11/1919 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 4/1984 |
| JP | 59-211459 | 11/1984 |
| JP | 59209608 | 11/1984 |
| JP | 59209609 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 07-083871 | 3/1995 |
| JP | 10-026601 | 1/1996 |
| JP | 8196626 | 8/1996 |
| WO | WO 1989-002720 | 4/1989 |
| WO | WO 1990-000738 | 1/1990 |
| WO | WO 1990-007575 | 7/1990 |
| WO | WO 1992-013271 | 8/1992 |
| WO | WO 1993-014185 | 7/1993 |
| WO | WO 1993-014693 | 8/1993 |
| WO | WO 1993-19701 | 10/1993 |
| WO | WO 1993-023744 | 11/1993 |
| WO | WO 1994-008236 | 4/1994 |
| WO | WO 1996-014026 | 5/1996 |
| WO | WO 1996-025088 | 8/1996 |
| WO | WO 1996-025089 | 8/1996 |
| WO | WO 1996-030431 | 10/1996 |
| WO | WO 1996-032076 | 10/1996 |
| WO | WO 1997-001986 | 1/1997 |
| WO | WO 1997-011067 | 3/1997 |
| WO | WO 1998-030891 | 7/1998 |
| WO | WO 1998-038906 | 9/1998 |
| WO | WO 1998-056293 | 12/1998 |
| WO | WO 1999-056613 | 4/1999 |
| WO | WO 2000-013003 | 3/2000 |
| WO | WO 2000-33065 | 8/2000 |
| WO | WO 2000-059373 | 10/2000 |
| WO | WO 2000-074753 | 12/2000 |
| WO | WO 2001-000865 | 1/2001 |
| WO | WO 2001-020019 | 3/2001 |
| WO | WO 2001-068901 | 9/2001 |
| WO | WO 2001-069222 | 9/2001 |
| WO | WO 2002-053764 | 7/2002 |
| WO | WO 2002-082989 | 10/2002 |
| WO | WO 2002-089666 | 11/2002 |
| WO | WO 2003-011131 | 2/2003 |
| WO | WO 2003-033726 | 4/2003 |
| WO | WO 2003-101862 | 12/2003 |

(56) References Cited

FOREIGN PATENT DOCUMENTS

| WO | WO 2005-045394 | 5/2005 |
|----|----------------|--------|
| WO | WO 2006-018425 | 2/2006 |
| WO | WO 2007-114943 | 10/2007 |

OTHER PUBLICATIONS

Kusano, Glucose enzyme electrode with percutaneous interface which operates independently of dissolved oxygen, 1989, Clin. Phys. Physiol. Meas., 10(1): 1-9.*
Aalders et al. 1991, Development of a wearable glucose sensor; studies in healthy volunteers and in diabetic patients. The International Journal of Artificial Organs 14(2):102-108.
Abe et al. 1992. Characterization of glucose microsensors for intracellular measurements. Analytical Chemistry 64(18):2160-2163.
Abel et al. 1984, Experience with an implantable glucose sensor as a prerequisite of an artificial beta cell. Biomedica et Biochimica Acta 43(5):577-584f.
Abel, P. U.; von Woedtke, T. 2002. Biosensors for in vivo glucose measurement: can we cross the experimental stage. Biosensors & Bioelectronics 17:1059-1070.
Alcock & Turner, 1994. Continuous Analyte Monitoring to Aid Clinical Practice. IEEE Engineering in Med. & Biol. 13:319-325.
American Heritage Dictionary, 4th Edition. 2000. Houghton Mifflin Company, p. 82.
Amin et al. 2003, Hypoglycemia prevalence in prepubertal children with type 1 diabetes on standard insulin regimen: Use of continuous glucose monitoring system. Diabetes Care 26(3):662-667.
Answers.com. "xenogenic." The American Heritage Stedman's Medical Dictionary. Houghton Mifflin Company, 2002. Answers. com Nov. 7, 2006 http:--www. Answers.com-topic-xenogenic.
Armour et al. Dec. 1990. Application of Chronic Intravascular Blood Glucose Sensor in Dogs. Diabetes 39:1519-1526.
Asberg et al. 2003. Hydrogels of a Conducting Conjugated Polymer as 3-D Enzyme Electrode. Biosensors & Bioelectronics 19:199-207.
Assolant-Vinet et al. 1986. New Immobilized Enzyme Membranes for Tailor-Made Biosensors, Anal Letters 19(7&8): 875-885.
Atanasov et al. 1997. Implantation of a refillable glucose monitoring-telemetry device. Biosensors & Bioelectronics 12:669-680.
Atanasov, et al. 1994. Biosensor for continuous glucose monitoring. Biotechnology and Bioengineering 43:262-266.
Aussedat et al. 1997. A user-friendly method for calibrating a subcutaneous glucose sensor-based hypoglycaemic alarm. Biosensors & Bioelectronics 12(11):1061-1071.
Bailey et al. 2007, Reduction in hemoglobin A1c with real-time continuous glucose monitoring: results from a 12-week observational study. Diabetes Technology & Therapeutics 9(3):203-210.
Baker R.W. 2008. Vapor and Gas Separation by Membranes—Advanced Membrane Technology and Applications [Eds. Li et al.], John Wiley & Sons, Inc., Chapter 21, pp. 559-580.
Bani Amer, M. M. 2002. An accurate amperometric glucose sensor based glucometer with eliminated crosssensitivity. J Med Eng Technol 26(5):208-213.
Beach et al. 1999. Subminiature implantable potentiostat and modified commercial telemetry device for remote glucose monitoring. IEEE Transactions on Instrumentation and Measurement 48(6):1239-1245.
Bellucci et al. Jan. 1986. Electrochemical behaviour of graphite-epoxy composite materials (GECM) in aqueous salt solutions. Journal of Applied Electrochemistry 16(1):15-22.
Bessman et al. 1973. Progress toward a glucose sensor for the artificial pancreas, Proceedings of a Workshop on Ion-Selective Microelectrodes, Jun. 4-5, 1973. Boston, MA, 189-197.
Biermann et al. 2008. How would patients behave if they were continually informed of their blood glucose levels? A simulation study using a "virtual" patient. Diabetes Technology & Therapeutics 10:178-187.
Bindra et al. 1989. Pulsed amperometric detection of glucose in biological fluids at a surface-modified gold electrode. Analytical Chemistry 61:2566-2570.
Bindra et al. 1991. Design and In Vitro Studies of a Needle-Type Glucose Sensor for Subcutaneous Monitoring. Analytical Chemistry 63:1692-96.
Bisenberger et al. 1995. A triple-step potential waveform at enzyme muitisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bobbioni-Harsch et al. 1993. Lifespan of subcutaneous glucose sensors and their performances during dynamic glycaemia changes in rats. J. Biomed. Eng. 15:457-463.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics 2(Suppl 1):S43-S48.
Bode, B. W. 2000. Clinical utility of the continuous glucose monitoring system. Diabetes Technology & Therapeutics, 2(Suppl 1):S35-S41.
Boedeker Plastics, Inc. 2009. Polyethylene Specifications Data Sheet, http:--www.boedeker.com-.polye_p.htm [Aug. 19, 2009 3:36:33 PM].
Boland et al. 2001, Limitations of conventional methods of self-monitoring of blood glucose. Diabetes Care 24(11):1858-1862.
Bott, A. W. 1997. A Comparison of Cyclic Voltammetry and Cyclic Staircase Voltammetry. Current Separations 16:1, 23-26.
Bowman, L.; Meindl, J. D. 1986. The packaging of implantable integrated sensors. IEEE Transactions on Biomedical Engineering BME33(2):248-255.
Brauker et al. 1995. Neovascularization of synthetic membranes directed by membrane Microarchitecture. J. Biomed. Mater. Res. 29:1517-1524.
Brauker et al, 1998. Sustained expression of high levels of human factor IX from human cells implanted within an immunoisolation device into athymic rodents. Hum Gene Therapy 9:879-888.
Brauker et al. 2001. Unraveling Mysteries at the Biointerface: Molecular Mediator of Inhibition of Blood vessel Formation in the Foreign Body Capsule Revealed. Surfacts. Biomaterials 6(3):1,5.
Brauker et al. Jun. 27, 1996. Local Inflammatory Response Around Diffusion Chambers Containing Xenografts. Transplantation 61(12):1671-1677.
Braunwald, 2008. Biomarkers in heart failure. N. Engl. J. Med. 358: 2148-2159.
Bremer et al. 2001. Benchmark data from the literature for evaluation of new glucose sensing technologies. Diabetes Technology & Therapeutics 3(3):409-418.
Brooks et al. 1987-88. Development of an on-line glucose sensor for fermentation monitoring. Biosensors 3:45-56.
Bruckel et al. 1989. In vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Analytical Chemistry 76(4):4038-4043.
Campanella et al. 1993. Biosensor for direct determination of glucose and lactate in undiluted biological fluids. Biosensors & Bioelectronics 8:307-314.
Candas et al (1994). An adaptive plasma glucose controller basedon on a nonlinear insulin-glucose model. IEEE Transactions on Biomedical Engineering 41(2):116-124.
Cass et al. 1984. Ferrocene-mediated enzyme electrodes for amperometric determination of glucose. Analytical Chemistry 36:667-71.
Cassidy et al., Apr. 1993. Novel electrochemical device for the detection of cholesterol or glucose. Analyst 118:415-418.

(56) References Cited

OTHER PUBLICATIONS

Cellulose Acetate Product Description, Product No. 419028, Sigma-Aldrich Corp., St. Louis, MO. 2005.
Chase et al. 2001. Continuous subcutaneous glucose monitoring in children with type 1 diabetes: Pediatrics 107:222-226.
Chatterjee et al. 1997. Poly(ether Urethane) and poly(ether urethane urea) membranes with high H2S-CH4 selectivity. Journal of Membrane Science 135:99-106.
Chen et al. 2006. A noninterference polypyrrole glucose biosensor. Biosensors and Bioelectronics 22:639-643.
Ciba® Irgacure 2959 Photoinitiator Product Description; Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al. 1987. Configurational cyclic voltammetry: increasing the specificity and reliablity of implanted electrodes. IEEE—Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
Clark et al., 1981, One-minute electrochemical enzymic assay for cholesterol in biological materials. Clinical Chemistry 27(12):1978-1982.
CLSI 208. Performance metrics for continuous interstitial glucose monitoring; approved guideline, CLSI document POCT05-A. Wayne, PA: Clinical and Laboratory Standards Institute POCT05A, 28(33), 72 pp.(2008).
Colangelo et al. 1967, Corrosion rate measurements in vivo, Journal of Biomedical Materials Research 1:405-414.
Colowick et al. 1976. Methods in Enzymology, vol. XLIV, Immobilized Enzymes. New York: Academic Press.
Cox et al, 1985. Accuracy of perceiving blood glucose in IDDM, Diabetes Care 8(6):529-536.
Csoregi et al., 1994. Design, characterization, and one-point in vivo calibration of a subcutaneously implanted glucose electrode. Analytical Chemistry 66(19):3131-3138.
Dai et al, 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors. Methods in Enzymology 137:181-197.
D'Arrigo et al. 2003. Porous-Si based bioreactors for glucose monitoring and drugs production. Proc. of SPIE 4982:178-184.
Dessau et al. 2009. In silico evaluation platform for artificial pancreatic (3-cell development—a dynamic simulator for closed loop control with hardware-in-the-loop. Diabetes Technology & Therapeutics, 11 (3):1-8.
Davies, et al. 1992. olymer membranes in clinical sensor applications. I. An overview of membrane function. Biomaterials 13(14):971-978.
Davis et al. 1983. Bioelectrochemical fuel cell and sensor based on a quinoprotein, alcohol dehydrogenase. Enzyme Microb. Technol., vol. 5, September, 383-388.
Decher et al. 1992. Buildup of ultrathin multilayer films by a self-assembly process: III. Consecutively alternating adsorption of anionic and cationic polyelectrolytes on charged surfaces. Thin Solid Films, 210-211:831-835.
Deutsch et al. 1994. Time series and control of blood glucose levels in diabetic patients. Computer Methods and Programs in Biomedicine 41 (1994) 167-182.
Direct 30-30® Blood Glucose Sensor, (Markwell Medical) Catalog, © 1990, ELCO Diagnostics Company.
Direct 30-30® meter (Markwell Medical) (Catalog).
Dixon et al. 2002. Characterization in vitro and in vivo of the oxygen dependence of an enzyme-polymer biosensor for monitoring brain glucose. Journal of Neuroscience Methods 119:135-142.
DuPont[1] Dimension AR® (Catalog), 1998.

Durliat et al. 1976. Spectrophotometric and electrochemical determinations of L(+)-lactate in blood by use of lactate dehydrogenase from yeast. Clinical Chemistry 22(11):1802-1805.
Edwards Lifesciences. Accuracy for your and your patients. Marketing materials, 4 pp. 2002.
Ekinci et al. 2006. Preparation and Characterization of an Aromatic Polyimide and Its Use as a Selective Membrane for H2O2. Turk J Chem. 30:277-285.
El Degheidy et al. 1986. Optimization of an implantable coated wire glucose sensor. Biomedical Engineering 8: 121-129.
El-Khatib et al. 2007. Adaptive closed-loop control provides blood-glucose regulation using dual subcutaneous insulin and glucagon infusion in diabetic swine, Journal of Diabetes Science and Technology 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Analytical and Bioanalytical Chemistry 373:758-761.
Fahy et al. Mar. 2008. An analysis: hyperglycemic intensive care patients need continuous glucose monitoring—easier said than done. Journal of Diabetes Science and Technology 2(2):201-204.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technology & Therapeutics 5(5):769-779.
Fischer et al. 1987. Assessment of subcutaneous glucose concentration: validation of the wick technique as a reference for implanted electrochemical sensors in normal and diabetic dogs. Diabetologia 30:940-945.
Fischer et al. 1989. Oxygen Tension at the Subcutaneous Implantation Site of Glucose Sensors. Biomed. Biochem 11-12:965-972.
Fischer et al. 1995. Hypoglycaemia-warning by means of subcutaneous electrochemical glucose sensors: an animal study. Horm. Metab. Rese. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diabetes Technology &Therapeutics 10:188-193.
Ganesan et al. 2005, Gold layer-based dual crosslinking procedure of glucose oxidase with ferrocene monocarboxylic acid provides a stable biosensor. Analytical Biochemistry 343:188-191.
Ganesh et al. Mar. 2008, Evaluation of the VIA® blood chemistry monitor for glucose in healthy and diabetic volunteers. Journal of Diabetes Science and Technology 2(2): 182-193.
Gao et al. 1989. Determination of Interfacial parameters of cellulose acetate membrane materials by HPLC. *J. Liquid Chromatography* 12(11):2083-2092.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.
Gerritsen et al. 2001. Influence of inflammatory cells and serum on the performance of implantable glucose sensors. J Biomed. Mater. Res. 54:69-75.
Gerritsen, M. 2000. Problems associated with subcutaneously implanted glucose sensors. Diabetes Care 23(2):143-145.

(56) References Cited

OTHER PUBLICATIONS

Gilligan et al. 1994. Evaluation of a subcutaneous glucose sensor out to 3 months in a dog model, Diabetes Care 17(8):882-887.
Gilligan et al. 2004, Feasibility of continuous long-term glucose monitoring from a subcutaneous glucose sensor in humans. Diabetes Technology & Therapeutics 6:378-386.
Godsland et al. 2001. Maximizing the Success Rate of Minimal Model Insulin Sensitivity Measurement in Humans: The Importance of Basal Glucose Levels. The Biochemical Society and the Medical Research Society, 1-9.
Gouda et al., Jul. 4, 2003. Thermal inactivation of glucose oxidase. The Journal of Biological Chemistry 278(27):24324-24333.
Gough et al. 2000, Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Analytical Chemistry 62:258-263.
Gross et al. 2000. Efficacy and reliability of the continuous glucose monitoring system. Diabetes Technology & Therapeutics 2(Suppl 1):S19-26.
Gross et al. 2000. Performance evaluation of the MiniMed® continuous glucose monitoring system during patient home use. Diabetes Technology & Therapeutics 2(1):49-56.
Guerci et al, 2003. Clinical performance of CGMS in type 1 diabetic patents treated by continuous subcutaneous insulin infusion using insulin analogs. Diabetes Care, 26:582-589.
Guo et al 1998. Modification of cellulose acetate ultrafiltration membrane by gamma ray radiation. Shuichuli Jishi Bianji Weiyuanhui, 23(6):315-318 (Abstract only).
Hall et al. 1998. Electrochemical oxidation of hydrogen peroxide at platinum electrodes, Part I: An adsorption-controlled mechanism. Electrochimica Acta 43(5-6):579-588.
Hall et al. 1998. Electrochemical oxidation of hydrogen peroxide at platinum electrodes, Part II: Effect of potential. Electrochimica Acta 43(14-15):2015-2024.
Hall et al. 1999. Electrochemical oxidation of hydrogen peroxide at platinum electrodes, Part III: Effect of temperature. Electrochimica Acta 44:2455-2462.
Hall et al. 1999. Electrochemical oxidation of hydrogen peroxide at platinum electrodes. Part IV: Phosphate buffer dependence. Electrochimica Acta 44:4573-4582.
Hall et al. 2000. Electrochemical oxidation of hydrogen peroxide at platinum electrodes. Part V: Inhibition by chloride. Electrochimica Acta 45:3573-3579.
Hamilton Syringe Selection Guide. 2006. Syringe Selection, www.hamiltoncompany.com.
Harrison et al. 1988, Characterization of perfluorosulfonic acid polymer coated enzyme electrodes and a miniaturized integrated potentiostat for glucose analysis in whole blood. Analytical Chemistry 60:2002-2007.
Hashiguchi et al. 1994..Development of a miniaturized glucose monitoring system by combining a needle-type glucose sensor with microdialysis sampling method: Long-term subcutaneous tissue glucose monitoring in ambulatory diabetic patients. Diabetes Care 17(5):387-396.
Heller 1990. Electrical wiring of redox enzymes. *Acc. Chem. Res.* 23:128-134.
Heller, A. 1992. Electrical Connection of Enzyme Redox Centers to Electrodes. J. Phys. Chem. 96:3579-3587.
Heiler, A. 1999. Implanted electrochemical glucose sensors for the management of diabetes. Annu Rev Biomedical Engineering 1:153-175.
Heiler, A. 2003. Plugging metal connectors into enzymes. Nature Biotechnology 21:631-632.
Hicks, 1985. In Situ Monitoring. Clinical Chemistry 31(12):1931-1935.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Analytical Chemistry 75:3308-3315.
http:--www.merriam-webster.com-dictionary. definition for "aberrant," Aug. 19, 2008, p. 1.
Hu, et al. 1993. A needle-type enzyme-based lactate sensor for in vivo monitoring. Analytica Chimica Acta 281:503-511.
Huang et al. 1997. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E. Final Technical Report to NASA, NASA-Ames Grant No. NGR 36-027-052.
Huang et al., "A 0.5mW Passive Telemetry IC for Biomedical Applications," Proceedings of the 23rd European Solid-State Circuits Conference (ESSCIRC '97), pp. 172-175, Sep. 1997, Southampton, UK.
Hunter et al. 2000. Minimally Invasive Glucose Sensor and Insulin Delivery System. MIT Home Automation and Healthcare Consortium. Progress Report No. 25.
Ishikawa, et al. 1998. Initial evaluation of a 290-mm diameter subcutaneous glucose sensor: Glucose monitoring with a biocompatible, flexible-wire, enzyme-based amperometric microsensor in diabetic and nondiabetic humans, Journal of Diabetes and Its Complications 12:295-301.
Jaffari et al. 1995. Recent advances in amperometric glucose biosensors for in vivo monitoring. Physiol. Meas. 16:1-15.
Jensen et al. 1997. Fast wave forms for pulsed electrochemical detection of glucose by incorporation of reductive desorption of oxidation products, Analytical Chemistry 69(9):1776-1781.
Jeutter, D. C. 1982. A transcutaneous implanted battery recharging and biotelemeter power switching system. IEEE Transactions on Biomedical Engineering 29:314-321.
Jobst et al. 2006. Thin-Film Microbiosensors for Glucose-Lactate Monitoring. Analytical Chemistry 8(18): 3173-3179.
Johnson 1991. Reproducible electrodeposition of biomolecules for the fabrication of miniature electroenzymatic biosensors. *Sensors and Actuators B* 5:85-89.
Johnson et al. 1992. In vivo evaluation of an electroenzymatic glucose sensor implanted in subcutaneous tissue, Biosensors & Bioelectronics 7:709-714.
Johnson, R.C. et al. 1997. Abstract: Neovascularization of cell transplantation devices: Role of membrane architecture and encapsulated tissue. Abstracts of Papers, American Chem. Soc. 214:2 P 305-PMSE.
Jovanovic, L. 2000. The role of continuous glucose monitoring in gestational diabetes mellitus. Diabetes Technology & Therapeutics 2(Suppl 1)S67-71.
Kacaniklic May-Jun. 1994. Amperometric Biosensors for Detection I- and D-Amino Acids based on Coimmobilized Peroxidase and L- and D-Amino Acid Oxidases in Carbon Paste Electrodes. Electroanalysis, 6(5-6):381-390.
Kamath et al. 2008. Calibration of a continuous glucose monitor: effect of glucose rate of change, Eighth Annual Diabetes Technology Meeting, Nov. 13-15, 2008, p. A88.
Kang et al. 2003. In vitro and short-term in vivo characteristics of a Kel-F thin film modified glucose sensor, Anal. Sci. 19:1481-1486.
Kargol et al. 2001. Studies on the structural properties of porous membranes: measurement of linear dimensions of solutes, Biophys Chem 91:263-271.
Karube et al. 1993. Microbiosensors for acetylcholine and glucose. Biosensors & Bioelectronics 8:219-228.
Kaufman et al. 2001. A pilot study of the continuous glucose monitoring system. Diabetes Care 24(12):2030-2034.

(56) References Cited

OTHER PUBLICATIONS

Kaufman. 2000. Role of the continuous glucose monitoring system in pediatric patients. Diabetes Technology & Therapeutics 2(Supp 1):S49-S52.
Kawagoe et al. 1991: Enzyme-modified organic conducting salt microelectrode, Analytical Chemistry 63:2961-2965.
Keedy et al. 1991. Determination of urate in undiluted whole blood by enzyme electrode. Biosensors & Bioelectronics 6: 491-499.
Kerner et al. 1988. A potentially implantable enzyme electrode for amperometric measurement of glucose. Horm Metab Res Suppl. 20:8-13.
Kerner et al. 1993. The function of a hydrogen peroxide-detecting electroenzymatic glucose electrode is markedly impaired in human sub-cutaneous tissue and plasma. Biosensors & Bioelectronics 8:473-482 (1993).
Kiechle, F.L. 2001. The impact of continuous glucose monitoring on hospital point-of-care testing programs. Diabetes Technology & Therapeutics 3:647-649.
Klueh et al. 2003. Use of Vascular Endothelia Cell Growth Factor Gene Transfer to Enhance Implantable Sensor Function In Vivo. J. Biomed. Mater. Res. 67A:1072-1086.
Klueh et al. 2007. Inflammation and glucose sensors: use of dexamethasone to extend glucose sensor function and life span in vivo. Journal of Diabetes Science and Technology 1(4):496-504.
Ko, Wen H. 1985. Implantable Sensors for Closed-Loop Prosthetic Systems, Future Pub. Co., Inc.; Mt. Kisco, NY, Chapter 15:197-210.
Kondo et al. 1982. A miniature glucose sensor, implantable in the blood stream. Diabetes Care. 5(3):218-221.
Koschinsky et al. 1988. New approach to technical and clinical evaluation of devices for self-monitoring of blood glucose. Diabetes Care 11(8): 619-619.
Koschinsky et al. 2001. Sensors for glucose monitoring: Technical and clinical aspects. Diabetes Metab. Res. Rev. 17:113-123.
Kost et al. 1985, Glucose-sensitive membranes containing glucose oxidase: activity, swelling, and permeability studies. Journal of Biomedical Materials Research 19:1117-1133.
Koudelka et al. 1989. In vivo response of microfabricated giucose sensors to glycemia changes in normal rats. Biomedica et Biochimica Acta 48(11-12):953-956.
Koudelka et al. 1991. In-vivo behaviour of hypodermically implanted microfabricated glucose sensors. Biosensors & Bioelectronics 6:31-36.
Kraver et al. 2001, A mixed-signal sensor interface microinstrument. Sensors and Actuators A 91:266-277.
Kruger et al. 2000. Psychological motivation and patient education: A role for continuous glucose monitoring. Diabetes Technology & Therapeutics 2(Suppl 1)S93-S97.
Kulys et al., 1994. Carbon-paste biosensors array for long-term glucose measurement. Biosensors & Bioelectronics, 9:491-500.
Kunjan et al., Automated blood sampling and glucose sensing in critical care settings, Journal of Diabetes Science and Technology 2(3): 194-200, Mar. 2008.
Kunzler et al. 1993. H ydrogels base on hydrophilic side chain siloxanes. Poly Mat Sci and Eng 69:226-227.
Kunzler et al. Aug. 21, 1995. Contact lens materials. Chemistry & Industry. 651-655.
Kurtz et al. 2005. Recommendations for blood pressure measurement in humans and experimental animals, Part 2: Blood pressure measurement in experimental animals, A statement for professionals from the subcommittee of professional and public education of . . . Hypertension 45:229-310.
Ladd et al. 1996. Structure Determination by X-ray Crystallography, 3rd ed. Plenum, 1996, Ch. 1, pp. xxi-xxiv and 1-58.
Lee et al. 1999. Effects of pore size, void volume, and pore connectivity on tissue responses. Society for Biomaterials 25th Annual Meeting, 171.
Lehmann et al. May 1994, Retrospective validation of a physiological model of glucose insulin interaction in type 1 diabetes mellitus. Med. Eng. Phys. 16:193-202.

Lerner et al. 1984. An implantable electrochemical glucose sensor. Ann. N. Y. Acad. Sci. 428:263-278.
Lewandowski et al. 1988. Evaluation of a miniature blood glucose sensor. Trans Am. Soc. Artif. Internal Organs 34:255-258.
Leypoldt et al. 1984. Model of a two-substrate enzyme electrode for glucose. A nalytical Chemistry 56:2896-2904.
Linke et al. 1994. Amperometric biosensor for in vivo glucose sensing based on glucose oxidase immobilized in a redox hydrogel. Biosensors & Bioelectronics 9:151-158.
Loffler et al. 1995. Separation and determination of traces of ammonia in air by means of chromatomembrane cells. Fresenius J Analytical Chemistry 352:613-614.
Lowe, 1984. Biosensors. Trends in Biotechnology 2(3):59-65.
Luong et al. 2004. Solubilization of Multiwall Carbon Nanotubes by 3-Aminopropyitriethcxysilane Towards the Fabrication of Electrochemical Biosensors with Promoted Electron Transfer. Electronanalysis 16(1-2):132-139.
Lyandres et al. (2008). Pregress toward an in vivo surface-enhanced raman spectroscopy glucose sensor. Diabetes Technology & Therapeutics, 10(4):257-265.
Lyman D. 1960. Polyurethanes. I. The Solution Polymerization of Diisocyanates with Ethylene Glycol. J. Polymer Sci. XLV:45:49.
Madaras, et al. 1996. Microfabricated amperometric creatine and creatinine biosensors. Analytics Chimica Acta 319:335-345.
Maidan et al, 1992. Elimination of Electrooxidizable Interferent-Produced Currents in Amperometric Biosensors. Analytical Chemistry 64:2889-2896.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: a multicenter analysis. Diabetes Care 25(2):347-352.
March; W. F. 2002. Dealing with the delay. Diabetes Technology & Therapeutics 4(1):49-50.
Marena et al. 1993. The artificial endocrine pancreas in clinical practice and research. Panminerva Medica 35(2):67-74.
Mascini et al. 1989. Glucose electrochemical probe with extended linearity for whole blood. J Pharm Biomed Anal 7(12): 1507-1512.
Mastrototaro et al. 1991. An electroenzymatic glucose sensor fabricated on a flexible substrate. Sensors and Actuators B 5:139-44.
Mastrototaro et al. 2003, Reproducibility of the continuous glucose monitoring system matches previous reports and the intended use of the product. Diabetes Care 26:256; author reply p. 257.
Mastrototaro; J. J. 2000. The MiniMed continuous glucose monitoring system. Diabetes Technology & Therapeutics 2(Suppl 1):S13-8.
Matsumoto et al. 1998. A micro-planar amperometeric glucose sensor unsusceptible to interference species. Sensors and Actuators B 49:68-72.
Matsumoto et al. 2001. A long-term lifetime amperometric glucose sensor with a perfluorocarbon polymer coating. Biosensors & Bioelectronics 16:271-276.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diabetes Technology & Therapeutics 10:149-159.
McCartney et al. 2001. Near-infrared fluorescence lifetime assay for serum glucose based on allophycocyanin-labeled concanavalin A. Analytical Biochemistry 292:216-221.
McGrath, M. J.; Iwuoha, E.I.; Diamond, D.; Smyth, M. R. 1995. The use of differential measurements with a glucose biosensor for interference compensation during glucose determinations by flow injection analysis. Biosensors & Bioelectronics 10:937-943.
McKean, et al. Jul. 7, 1988. A Telemetry Instrumentation System for Chronically Implanted Glucose and Oxygen Sensors. Transactions on Biomedical Engineering 35:526-532.

(56) References Cited

OTHER PUBLICATIONS

Memoli et al. 2002, A comparison between different immobilised glucoseoxidase-based electrodes. J Pharm Biomed Anal 29:1045-1052.
Merriam-Webster Online Dictionary. Definition of "acceleration". http:--www.merriam-webster.com-dictionary-Acceleration Jan. 11, 2010.
Merriam-Webster Online Dictionary. Definition of "nominal." http:--www.m-w.com-dictionary-nominal Apr. 23, 2007.
Merriam-Webster Online Dictionary. Definition of "system." http:--www.merriam- webster.com-dictionary-System Jan. 11, 2010.
Merriam-Webster Online Dictionary. The term "nominal." http:--www.m-w.com-dictionary-nominal.
Meyerhoff et al. 1992. On line continuous monitoring of subcutaneous tissue glucose in men by combining portable glucosensor with microdialysis. Diabetologia 35:1087-1092.
Miller et al. 1989. Generation of IL1-like activity in response to biomedical polymer implants: a comparison of in vitro and in vivo models. J Biomed Mater Res 23:1007-1026.
Miller et al. 1989. In vitro stimulation of fibroblast activity by factors generated from human monocytes activated by biomedical polymers. J Biomed Mater Res 23:911-930.
Miller, A. 1988. Human monocyte-macrophage activation and interleukin 1 generation by biomedical polymers. J Biomed Mater Res 23:713-731.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al. Jun. 1994. Reduction of acetaminophen interference in glucose sensors by a composite Nation membrane: demonstration in rats and man. Diabetologia 37(6):610-616.
Moatti-Sirat, D, et al. 1992. Evaluating in vitro and in vivo the interference of ascorbate and acetaminophen on glucose detection by a needle-type glucose sensor. Biosensors and Bioelectronics 7:345-352.
Morff et al. 1990. Microfabrication of reproducible, economical, electroenzymatic glucose sensors. Annual International Conference of the IEEE Engineering in Medicine and Biology Society 12(2):0483-0484.
Mosbach et al. 1975. Determination of heat changes in the proximity of immobilized enzymes with an enzyme termistor and its use for the assay of metabolites. Biochimica et Biophysics Acta. (Enzymology) 403:256-265.
Motonaka et al. 1993. Determination of cholesterol and cholesterol ester with novel enzyme microsensors, Analytical Chemistry 65:3258-3261.
Moussy et al. 1993. Performance of subcutaneously implanted needle-type glucose sensors employing a novel trilayer coating. Analytical Chemistry 85: 2072-2077.
Moussy et al. 2000. Biomaterials community examines biosensor biocompatibility. Diabetes Technology & Therapeutics 2:473-477.
Moussy, Francis, Nov. 2002, Implantable Glucose Sensor: Progress and Problems. Sensors 1:270-273.
Mowery et al, 2000. Preparation and characterization of hydrophobic polymeric films that are thromboresistant via nitric oxide release. Biomaterials 21:9-21.
Murphy, et al. 1992. Polymer membranes in clinical sensor applications. II. The design and fabrication of permselective hydrogels for electrochemical devices. Biomaterials 13(14):979-990.
Muslu, 1991. Trickling filter performance. Applied Biochemistry and Biotechnology 37:211-224.
Myler et al. 2002. Ultra-thin-polysiloxane-film-composite membranes for the optimisation of amperometric oxidase enzyme electrodes. Biosensors & Bioelectronics 17:35-43.
Nafion® 117 Solution Product Description, Product No. 70160, Sigma-Aldrich Corp., St. Louis, MO.
Nakayama et al. 1992. Surface fixation of hydrogels: heparin and glucose oxidase hydrogelated surfaces. ASAIO Journal 38:M421-M424.
Nam et al. 2000. A novel fabrication method of macroporous biodegradable polymer scaffolds using gas foaming salt as a porogen additive. J Biomed Mater Res 53:1-7.
Nation® 117 Solution Product Description, Product No. 70160, Sigma-Aldrich Corp., St. Louis, MO. Apr. 7, 2005.
Ohara, et al. Dec. 1993. Glucose electrodes based on cross-linked bis(2,2'-bipyridine)chloroosmium(+-2+) complexed poly(l-vinylimidazole) films, Analytical Chemistry, 65:3512-3517.
Ohara, T. J.; Rajagopalan, R.; Heller, A. 1994. "Wired" enzyme electrodes for amperometric determination of glucose or lactate in the presence of interfering substances, Analytical Chemistry 66:2451-2457.
Okuda et al. 1971. Mutarotase effect on micro determinations of D-glucose and its anomers with (3- D-glucose oxidase. Analytical Biochemistry 43:312-315.
Oxford English Dictionary Online. Definition of "impending". http:--www.askoxford.com-results-?view=dev dict&field-12668446 Impending&branch= Jan. 11, 2010.
Palmisano, et al. 2000. Simultaneous monitoring of glucose and lactate by an interference and cross-talk free dual electrode amperometric biosensor based on electropolymerized thin films. Biosensors & Bioelectronics 15:531-539.
Panetti 2002. Differential effects of sphingosine 1-phosphate and lysophosphatidic acid on endothelial cells. Biochimica et Biophysica Acta 1582:190-196.
Park et al. 2002. Gas separation properties of polysiloxane-polyether mixed soft segment urethane urea membranes, J. Membrane Science 204:257-269.
Patel et al. 2003. Amperometric glucose sensors based on ferrocene containing polymeric electron transfer systems—a preliminary report. Biosensors & Bioelectronics 18:1073-6.
Peacock et al. 2008. Cardiac troponin and outcome in acute heart failure. N. Engl. J. Med. 358:2117-2126.
Pecoraro et al. 1995. Gas transport properties of siloxane polyurethanes. Journal of Applied Polymer Science 57:421-429.
Pfeiffer et al. 1992. On line continuous monitoring of subcutaneous tissue glucose is feasible by combining portable glucosensor with microdialysis. Horm. Metab. Res. 25:121-124.
Pfeiffer, E.F. 1990. The glucose sensor, the missing link in diabetes therapy. Horm Metab Res Suppl. 24:154-164.
Phillips and Smith 1988. Biomedical Applications of Polyurethanes: implications of Failure Mechanisms. J. Biomat, Appl. 3:202-227.
Pichert et al. 2000. Issues for the coming age of continuous glucose monitoring. Diabetes Educator 26(6):969-980.
Pickup et al. 1987-88. Implantable glucose sensors: choosing the appropriate sensor strategy. Biosensors 3:335-346(1987-88).
Pickup et al. 1988. Progress towards in vivo glucose sensing with a ferrocene-mediated amperometric enzyme electrode, Horm. Metab. Res. Supp. 20:34-36.
Pickup et al. 1989. In vivo molecular sensing in diabetes mellitus: an implantable glucose sensor with direct electron transfer. Diabetologia 32:213-217.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK). TIBTECH 11: 285-291.
Pickup, etal. 1993. Responses and Calibration of Amperometric Glucose Sensors Implanted in the Subcutaneous Tissue of Man. ACTA Diabetologia 30:143-148.
Pineda et al. 1996. Bone regeneration with resorbable polymeric membranes. III. Effect of poly(L-lactide) membrane pore size on the bone healing process in large defects. J. Biomedical Materials Research 31:385-394
Pinner et al. 1959. Cross-linking of cellulose acetate by ionizing radiation. Nature 184:1303-1304.
Pishko et al. 1991. Amperometric glucose microelectrodes prepared through immobilization of glucose oxidase in redox hydrogels. Analytical Chemistry 63:2268-2272.
Pitzer et al. 2001. Detection of hypoglycemia with the GlucoWatch biographer. Diabetes Care 24(5):881-885.
Poitout et al. 1993. A glucose monitoring system for on line estimation in man of blood glucose concentration using a minia-

(56) References Cited

OTHER PUBLICATIONS turized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Poitout, et al. 1991. In Vitro and In Vivo Evaluation in Dogs of a Miniaturized Glucose Sensor, ASAIO Transactions 37:M298-M300.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981, Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn, C. A.; Connor, R. E.; Heller, A. 1997. Biocompatible, glucose-permeable hydrogel for in situ coating of implantable biosensors. Biomaterials 18:1665-1670.
Rabahetal., 1991. Electrochemical wear of graphite anodes during electrolysis of brine. Carbon 29(2):165-171.
Ratner, B.D. 2002, Reducing capsular thickness and enhancing angiogenesis around implant drug release systems, J Control Release 78:211-218.
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000, 2:49-56. Diabetes Technology & Therapeutics 3(1):129-130.
Rebrin et al. 1989. Automated feedback control of subcutaneous glucose concentration in diabetic dogs. Diabetologia 32:573-76.
Rebrin et al. 1992. Subcutaneous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16, http:--www.cem.msu.edu-~reusch-VirtualText-orgmetal.htm.
Rhodes, et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diabetes Technology & Therapeutics 10:194-199.
Rivers et al. 2001. Central venous oxygen saturation monitoring in the critically ill patient. Current Opinion in Critical Care 7:204-211.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sakakida, et al, 1992. Development of Ferrocene-Mediated Needle-Type Glucose Sensor as a Measure of True Subcutaneous Tissue Glucose Concentrations. Artif. Organs Today 2(2): 145-158.
Sakakida, et al. 1993. Ferrocene-Mediated Needle Type Glucose Sensor Covered with Newly Designed Biocompatible Membrane. Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10):1840-1844.
Samuels, M.P. 2004. The effects of flight and altitude. Arch Dis Child. 89:448-455.
San Diego Plastics, Inc. 2009, Polyethylene Data Sheet, http:--www.sdplastics.com-polyeth.html.
Sanders et al. Dec. 2003. Fibrous Encapsulation of Single Polymer Microfibers Depends on their Vertical Dimension in subcutaneous Tissue. J. Biomedical Materials Research A 67(4):1181-1187.
Sansen et al. 1985. Glucose sensor with telemetry system. In Ko, W. H. (Ed.), Implantable Sensors for Closed Loop Prosthetic Systems, Future Publishing Co., Mount Kisco, NY. Chap. 12, pp. 167-175.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. 1998. Measurement and modeling of the transient difference between blood and subcutaneous glucose concentrations in the rat after injection of insulin. PNAS USA 95:294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO Journal 43:137-142.
Service et al. 1970. Mean amplitude of glycemic excursions, a measure of diabetic instability, Diabetes 19:644-655.
Service et al. 1987. Measurements of glucose control. Diabetes Care 10:225-237.
Service, R. F. 2002. Can sensors make a home in the body? Science 297:962-963.
Sharkawy et al. 1996, Engineering the tissue which encapsulates subcutaneous implants. I. Diffusion properties. J. Biomed Mater Res 37:401-412.
Shaw et al. 1991. In vitro testing of a simply constructed, highly stable glucose sensor suitable for implantation in diabetic patients. Biosensors & Bioelectronics 6:401-406.
Shichiri, et al. 1983. Glycaemic Control in Pancreatectomized Dogs with a Wearable Artificial Endocrine Pancreas, Diabetologia 24:179-184.
Shichiri, et al. 1986, Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri, et al., 1989. Membrane Design for Extending the Long-Life of an Implantable Glucose Sensor. Diabetes Nutr. Metab, 2:309-313.
Shichiri, M.; Kawamori, R.; Yamasaki, Y.; Hakui, N.; Abe, H. 1982. Wearable artificial endocrine pancrease with needle-type glucose sensor. Lancet 2:1129-1131.
Shichiri, M.; Kawamori, R.; Yamasaki, Y.; Hakui, N.; Asakawa, N.; Abe; H. 1985. Needle-type Glucose Sensor for Wearable Artificial Endocrine Pancreas in Implantable Sensors, Chapter 15, pp. 197-210 in Implantable Sensors for Closed-Loop Prosthetic Systems 197-210, Ed. Wen H. Ko et al., Future Publishing Company, Inc., Mount Kisco, NY.
Shults et al. 1994. A telemetry-instrumentation system for monitoring multiple subcutaneously implanted glucose sensors. IEEE Transactions on Biomedical Engineering 41(10):937-942.
Sieminski et al. 2000. Biomaterial-microvasculature interactions. Biomaterials 21:2233-2241.
Skyler, J. S. 2000. The economic burden of diabetes and the benefits of improved glycemic control: The potential role of a continuous glucose monitoring system. Diabetes Technology & Therapeutics 2(Suppl 1):S7-12.
Slater-Maclean et al. 2008. Accuracy of glycemic measurements in the critically ill. Diabetes Technology & Therapeutics 10:169-177.
Smith et al. 1991. A Comparison of Islet Transplantation and Subcutaneous Insulin Injections for the Treatment of Diabetes Mellitus, Comput. Biol. Med. 21(6):417-427.

(56) References Cited

OTHER PUBLICATIONS

Sokol et al. 1980. Immobilized-enzyme rate-determination method for glucose analysis. Clinical Chemistry 26(1):89-92.
Sriyudthsak, M.; Cholapranee, T.; Sawadsaringkarn, M.; Yupongchaey, N.; Jaiwang, P. 1996. Enzyme-epoxy membrane based glucose analyzing system and medical applications. Biosensors & Bioelectronics 11:735-742.
Steil et al. 2003. Determination of plasma glucose during rapid glucose excursions with a subcutaneous glucose sensor. Diabetes Technology & Therapeutics 5(1 ):27-31.
Stern et al., 1957. Electrochemical polarization: 1. A theoretical analysis of the shape of polarization curves. Journal of the Electrochemical Society 104(1 ):56-63.
Sternberg et al. 1988. Covalent enzyme coupling on cellulose acetate membranes for glucose sensor development. Analytical Chemistry 69:2781-2786.
Sternberg, et al. 1988. Study and Development of Multilayer Needle-type Enzyme-based Glucose Microsensors. Biosensors 4:27-40.
Stokes. 1988. Polyether Polyurethanes: Biostable or Not? J. Biomat. Appl. 3:228-259.
Street et al. Dec. 2004, Islet Graft Assessment in the Edmonton Protocol: Implications for Predicting Long-Term Clinical Outcome. Diabetes 53:3107-3114.
Suh et al. 2002, Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE 20(4):1775-1778.
Takegami et al. 1992. Pervaporation of ethanol water mixtures using novel hydrophobic membranes containing polydimethylsiloxane. Journal of Membrane Science 75(93-105).
Tanenberg et al. 2000. Continuous glucose monitoring system: A new approach to the diagnosis of diabetic gastroparesis. Diabetes Technology & Therapeutics 2(Suppl 1):S73-S80.
Tang et al. 1993. Fibrin(ogen) mediates acute inflammatory responses to biomaterials. J Exp Med 178:2147-2156.
Tang et al. 1995, Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. PNAS USA 95:8841-8846.
Tatsuma et al. 1991. Oxidase-peroxidase bilayer-modified electrodes as sensors for lactate, pyruvate, cholesterol and uric acid. Analytics Chimica Acta; 242:65-89.
Thom6-Duret, et al. 1996. Modification of the sensitivity of glucose sensor implanted into subcutaneous tissue. Diabetes Metabolism 22:174-178.
Thome et al. 1995. Abstract—Can the decrease in subcutaneous glucose concentration precede the decrease in blood glucose level? Proposition for a push-pull kinetics hypothesis. Horm. Metab. Res. 27:53.
Thome-Duret et al. 1996. Modification of the sensitivity of glucose sensor implanted into subcutaneous tissue. Diabetes Metabolism 22:174-178.
Thome-Duret et al. 1998. Continuous glucose monitoring in the free-moving rat, Metabolism 47:799-803.
Thompson et al. 1986. In Vivo Probes: Problems and Perspectives, Department of Chemistry, University of Toronto, Canada, pp. 255-261.
Tibell et al. 2001. Survival of macroencapsulated allogeneic parathyroid tissue one year after transplantation in nonimmunosuppressed humans. Cell Transplant 10:591-599.
Tierney et al, 2000. The GlucoWatch® biographer: A frequent, automatic and noninvasive glucose monitor, Ann. Med. 32:632-641.
Torjman et al. Mar. 2008. Glucose monitoring in acute care: technologies on the horizon. Journal of Diabetes Science and Technology 2(2):178-181.
Trecroci, D. 2002. A Glimpse into the Future—Continuous Monitoring of Glucose with a Microfiber. Diabetes Interview 42-43.
Tse and Gough. 1987. Time-Dependent inactivation of Immobilized Glucose Oxidase and Catalase. Biotechnol. Bioeng. 29:705-713.
Turner and Pickup 1985. Diabetes mellitus: biosensors for research and management. *Biosensors* 1:85-115(1985).
Turner et al. 1984. Carbon Monoxide: Acceptor Oxidoreductase from Pseudomonas Thermocarboxydovorans Strain C2 and its use in a Carbon Monoxide Sensor. Analytica Chimica Acta 163: 161-174.
Turner, A.P.F. 1988. Amperometric biosensor based on mediator-modified electrodes. Methods in Enzymology 137:90-103.
Unger et al. 2004. Glucose control in the hospitalized patient. Emergency Med 36(9):12-18.
Updike et al. 1967. The enzyme electrode. Nature 214:986-988.
Updike et al. 1988. Laboratory Evaluation of New Reusable Blood Glucose Sensor. Diabetes Care 11:801-807.
Updike et al. 1994. Enzymatic glucose sensor: Improved long-term performance in vitro and in vivo. ASAIO Journal 40(2): 157-163.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York, John Wiley & Sons, pp. 117-137.
Updike, et al. 1982. Implanting the glucose enzyme electrode: Problems, progress, and alternative solutions. Diabetes Care 5(3):207-212.
Updike, et al. 2000. A subcutaneous glucose sensor with improved longevity, dynamic range, and stability of calibration. Diabetes Care 23(2):208-214.
Utah Medical Products Inc., Blood Pressure Transducers product specifications, 6 pp. 2003-2006, 2003.
Vadgama, P. Nov. 1981. Enzyme electrodes as practical biosensors. Journal of Medical Engineering & Technology 5(6):293-298.
Vadgama, 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clinic Proceedings 79(8):977-978.
Velho et al. 1989, Strategies for calibrating a subcutaneous glucose sensor. Biomed Biochim Acta 48(11-12):957-964.
von Woedtke et al. 1989. In situ calibration of implanted electrochemical glucose sensors. Biomed Biochim. Acta 48(11-12):943-952.
Wade Jr., L.G. 1987. Organic Chemistry, Chapter 17, Reactions of Aromatic Compounds pp. 762-763.
Wagner, et al. 1998. Continuous amperometric monitoring of glucose in a brittle diabetic chimpanzee with a miniature subcutaneous electrode. PNAS USA 95:6379-6382.
Wang et al. 1994. Highly Selective Membrane-Free, Mediator-Free Glucose Biosensor. Analytical Chemistry 66:3600-3603.
Wang et al. 1997. Improved ruggedness for membrane-based amperometric sensors using a pulsed amperometric method. Analytical Chemistry 69:4482-4489.
Wang, J. 2007. Electrochemical Glucose Biosensor. American Chemical Society, Chemical Reviews, Published on Web Dec. 23, 2007, page est. 11.1, pp. 1-12; 10.1021-cr068123a.
Ward et al. 2000. Rise in background current overtime in a subcutaneous glucose sensor in the rabbit: Relevance to calibration and accuracy. Biosensors & Bioelectronics 15:53-61.
Ward et al. 2002. A new amperometric glucose microsensor in vitro and short-term in vivo evaluation, Biosensors & Bioelectronics, 17:181-189.
Ward et al. 2004. A wire-based dual-analyte sensor for Glucose and Lactate: In Vitro and In Vivo Evaluation. Diabetes Technology & Therapeutics 6(3):389-401.
Ward, W. K.; Wood, M. D.; Troupe, J. E. 2000. Understanding Spontaneous Output Fluctuations of an Amperometric Glucose Sensor: Effect of Inhalation Anesthesia and e of a Nonenzyme Containing Electrode. ASAIO Journal 46:540-546.
Wientjes, K. J. C. 2000. Development of a glucose sensor for diabetic patients (Ph.D. Thesis).
Wikipedia 2006. "Intravenous therapy," http:--en.wikipedia.org-wiki-Intravenous_therapy, Aug. 15, 2006, 6 pp.

(56) References Cited

OTHER PUBLICATIONS

Wiley Electrical and Electronics Engineering Dictionary. 2004. John Wiley & Sons, Inc. pp. 141, 142, 548, 549.
Wilkins et al. 1988, The coated wire electrode glucose sensor. Horm Metab Res Suppl. 20:50-55.
Wilkins et al. 1995, Integrated implantable device for long-term glucose monitoring. Biosensors & Bioelectronics. 10;485-494.
Wilkins, E.; Atanasov, P. 1996. Glucose monitoring: state of the art and future possibilities. Med Eng Phys 18:273- 288.
Wilson et al. 1992, Progress toward the development of an implantable sensor for glucose. Clinical Chemistry 38(9):1613-1617.
Wilson, et al. 2000, Enzyme-based biosensors for in vivo measurements. Chem. Rev. 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor, Diabetes Care 5:278-281.
Worsley et al. Mar. 2008. Measurement of glucose in blood with a phenylboronic acid optical sensor, Journal of Diabetes Science and Technology 2(2):213-220.
Wright et al. 1999. Bioelectrochemical dehalogenations via direct electrochemistry of poly(ethylene oxide)—modified myoglobin. Electrochemistry Communications 1:603-611.
Wu et al. 1999. In situ electrochemical oxygen generation with an immunoisolation device. Annals New York Academy of Sciences pp. 105-125.
Yamasaki et al. 1989. Direct measurement of whole blood glucose by a needle-type sensor, Clinica Chimica Acta. 93:93-98.
Yamasaki, Yoshimitsu. Sep. 1984. The development of a needle-type glucose sensor for wearable artificial endocrine pancreas. Medical Journal of Osaka University 35(1-2):25-34.
Yang et al (1996). A glucose biosensor based on an oxygen electrode: In-vitro performances in a model buffer solution and in blood plasma. Biomedical Instrumentation & Technology 30:55-61.
Yang et al. 1997. Polyelectrolyte and molecular host ion self-assembly to multilayer thin films: An approach to thin film chemical sensors. Sensors & Actuators B 45:87-92.
Yang, et al. 1998. Development of needle-type glucose sensor with high selectivity. Science and Actuators B 46:249-256.
Yang, et al. 2004. A Comparison of Physical Properties and Fuel Cell Performance of Nation and Zirconium Phosphate-Nafion Composite Membranes, Journal of Membrane Science 237:145-161.
Ye et al. 1993. High Current Density 'Wired' Quinoprotein Glucose Dehydrogenase Electrode. Analytical Chemistry 65:238-241.
Zamzow et al. 1990. Development and evaluation of a wearable blood glucose monitor. ASAIO Transactions 36(3): pp. M588-M591.
Zethelius et al. 2008. Use of multiple biomarkers to improve the prediction of death from cardiovascular causes. N. Engl. J. Med. 358: 2107-2116.
Zhang et al (1993). Electrochemical oxidation of H2O2 on Pt and Pt + Ir electrodes in physiological buffer and its applicability to H2O2-based biosensors. J. ElectroAnalytical Chemistry 345:253-271.
Zhang et al. 1993. In vitro and in vivo evaluation of oxygen effects on a glucose oxidase based implantable glucose sensor. Analytica Chimica Acta 281:513-520.
Zhang, et al. 1994. Elimination of the acetaminophen interference in an implantable glucose sensor. Analytical Chemistry 66(7):1183-1188.
Zhu et al. (1994). Fabrication and characterization of glucose sensors based on a microarray H2O2 electrode. Biosensors & Bioelectronics 9: 295-300.
Zhu, et al. 2002. Planar amperometric glucose sensor based on glucose oxidase immobilized by chitosan film on Prussian blue layer. Sensors 2:127-136.
PCT/US06/016515, filed Apr. 28, 2006: International Preliminary Report on Patentability dated Nov. 16, 2007.
U.S. Appl. No. 09/447,227, filed Nov. 22, 1999, Issued as U.S. Pat. No. 8,527,025 on Sep. 3, 2013: Office Action dated Aug. 15, 2001.
U.S. Appl. No. 09/447,227, filed Nov. 22, 1999, Issued as U.S. Pat. No. 8,527,025 on Sep. 3, 2013: Office Action dated Jan. 17, 2002.
U.S. Appl. No. 09/447,227, filed Nov. 22, 1999, Issued as U.S. Pat. No. 8,527,025 on Sep. 3, 2013: Office Action dated Jul. 15, 2002.
U.S. Appl. No. 09/447,227, filed Nov. 22, 1999, Issued as U.S. Pat. No. 8,527,025 on Sep. 3, 2013: Office Action dated Jan. 16, 2003.
U.S. Appl. No. 09/447,227, filed Nov. 22, 1999, Issued as U.S. Pat. No. 8,527,025 on Sep. 3, 2013: Office Action dated Jul. 9, 2003.
U.S. Appl. No. 09/447,227, filed Nov. 22, 1999, Issued as U.S. Pat. No. 8,527,025 on Sep. 3, 2013: Office Action dated Nov. 28, 2003.
U.S. Appl. No. 09/447,227, filed Nov. 22, 1999, Issued as U.S. Pat. No. 8,527,025 on Sep. 3, 2013: Office Action dated Sep. 22, 2005.
U.S. Appl. No. 09/447,227, filed Nov. 22, 1999, Issued as U.S. Pat. No. 8,527,025 on Sep. 3, 2013: Office Action dated Apr. 4, 2006.
U.S. Appl. No. 09/447,227, filed Nov. 22, 1999, Issued as U.S. Pat. No. 8,527,025 on Sep. 3, 2013: Office Action dated Aug. 1, 2006.
U.S. Appl. No. 09/447,227, filed Nov. 22, 1999, Issued as U.S. Pat. No. 8,527,025 on Sep. 3, 2013: Office Action dated Mar. 9, 2007.
U.S. Appl. No. 09/447,227, filed Nov. 22, 1999, Issued as U.S. Pat. No. 8,527,025 on Sep. 3, 2013: Office Action dated Jul. 17, 2007.
U.S. Appl. No. 09/447,227, filed Nov. 22, 1999, Issued as U.S. Pat. No. 8,527,025 on Sep. 3, 2013: Office Action dated Jan. 23, 2008.
U.S. Appl. No. 09/447,227, filed Nov. 22, 1999, Issued as U.S. Pat. No. 8,527,025 on Sep. 3, 2013: Office Action dated Jun. 12, 2008.
U.S. Appl. No. 09/447,227, filed Nov. 22, 1999, Issued as U.S. Pat. No. 8,527,025 on Sep. 3, 2013: Office Action dated Dec. 11, 2008.
U.S. Appl. No. 09/447,227, filed Nov. 22, 1999, Issued as U.S. Pat. No. 8,527,025 on Sep. 3, 2013: Office Action dated May 26, 2009.
U.S. Appl. No. 09/447,227, filed Nov. 22, 1999, Issued as U.S. Pat. No. 8,527,025 on Sep. 3, 2013: Office Action dated Dec. 6, 2009.
U.S. Appl. No. 09/447,227, filed Nov. 22, 1999, Issued as U.S. Pat. No. 8,527,025 on Sep. 3, 2013: Office Action dated Jan. 14, 2010.
U.S. Appl. No. 09/916,711, filed Jul. 27, 2001: Office Action dated Jul. 1, 2005.
U.S. Appl. No. 09/916,711, filed Jul. 27, 2001: Office Action dated Sep. 5, 2006.
U.S. Appl. No. 09/916,711, filed Jul. 27, 2001: Office Action dated Feb. 11, 2004.
U.S. Appl. No. 09/916,711, filed Jul. 27, 2001: Office Action dated Feb. 14, 2006.
U.S. Appl. No. 09/916,711, filed Jul. 27, 2001: Office Action dated Dec. 23, 2004.
U.S. Appl. No. 09/916,711, filed Jul. 27, 2001: Office Action dated Jul. 23, 2004.
U.S. Appl. No. 09/916,711, filed Jul. 27, 2001: Office Action dated Sep. 24, 2003.
U.S. Appl. No. 10/153,356, filed May 22, 2002, Issued as U.S. Pat. No. 7,226,978 on Jun. 5, 2007: Office Action dated Feb. 17, 2004.
U.S. Appl. No. 10/153,356, filed May 22, 2002, Issued as U.S. Pat. No. 7,226,978 on Jun. 5, 2007: Office Action dated Aug. 12, 2004.
U.S. Appl. No. 10/153,356, filed May 22, 2002, Issued as U.S. Pat. No. 7,226,978 on Jun. 5, 2007: Office Action dated Mar. 15, 2005.
U.S. Appl. No. 10/153,356, filed May 22, 2002, Issued as U.S. Pat. No. 7,226,978 on Jun. 5, 2007: Office Action dated Oct. 6, 2005.
U.S. Appl. No. 10/153,356, filed May 22, 2002, Issued as U.S. Pat. No. 7,226,978 on Jun. 5, 2007: Office Action dated Mar. 10, 2006.
U.S. Appl. No. 10/153,356, filed May 22, 2002, Issued as U.S. Pat. No. 7,226,978 on Jun. 5, 2007: Office Action dated Aug. 29, 2006.
U.S. Appl. No. 10/153,356, filed May 22, 2002, Issued as U.S. Pat. No. 7,226,978 on Jun. 5, 2007: Office Action dated Mar. 7, 2007.
U.S. Appl. No. 10/695,636, filed Oct. 28, 2003, now abandoned: Office Action dated Dec. 6, 2005.
U.S. Appl. No. 10/695,636, filed Oct. 28, 2003, now abandoned: Office Action dated May 22, 2006.
U.S. Appl. No. 10/695,636, filed Oct. 28, 2003, now abandoned: Office Action dated Mar. 14, 2007.
U.S. Appl. No. 10/838,658, filed May 3, 2004, issued as U.S. Pat. No. 8,277,713 Oct. 2, 2012: Office Action dated Dec. 15, 2008.
U.S. Appl. No. 10/838,658, filed May 3, 2004, issued as U.S. Pat. No. 8,277,713 Oct. 2, 2012: Office Action dated Jul. 30, 2009.

(56) References Cited

OTHER PUBLICATIONS

U.S. Appl. No. 10/838,658, filed May 3, 2004, issued as U.S. Pat. No. 8,277,713 Oct. 2, 2012: Office Action dated Mar. 30, 2010.
U.S. Appl. No. 10/885,476, filed Jun. 6, 2004, now abandoned: Office Action dated Dec. 24, 2008.
U.S. Appl. No. 10/885,476, filed Jul. 6, 2004, now abandoned: Office Action dated Jun. 23, 2009.
U.S. Appl. No. 10/896,639, filed Jul. 21, 2004, issued as U.S. Pat. No. 7,379,765 on May 27, 2008: Office Action dated Sep. 23, 2005.
U.S. Appl. No. 10/896,639, filed Jul. 21, 2004, issued as U.S. Pat. No. 7,379,765 on May 27, 2008: Office Action dated Apr. 6, 2006.
U.S. Appl. No. 10/896,639, filed Jul. 21, 2004, issued as U.S. Pat. No. 7,379,765 on May 27, 2008: Office Action dated Aug. 22, 2006.
U.S. Appl. No. 10/896,639, filed Jul. 21, 2004, issued as U.S. Pat. No. 7,379,765 on May 27, 2008: Office Action dated Apr. 11, 2007.
U.S. Appl. No. 10/896,639, filed Jul. 21, 2004, issued as U.S. Pat. No. 7,379,765 on May 27, 2008: Office Action dated Oct. 5, 2007.
U.S. Appl. No. 10/991,353, filed Nov. 16, 2004, now abandoned: Office Action dated Sep. 12, 2008.
U.S. Appl. No. 10/991,353, filed Nov. 16, 2004, now abandoned: Office Action dated Mar. 14, 2009.
U.S. Appl. No. 10/991,353, filed Nov. 16, 2004, now abandoned: Office Action dated Jul. 31, 2009.
U.S. Appl. No. 10/991,353, filed Nov. 16, 2004, now abandoned: Office Action dated Jan. 14, 2010.
U.S. Appl. No. 11/077,693, filed Mar. 10, 2005, issued as U.S. Pat. No. 7,713,574 on May 1, 2010: Office Action dated Jun. 27, 2008.
U.S. Appl. No. 11/077,693, filed Mar. 10, 2005, issued as U.S. Pat. No. 7,713,574 on May 11, 2010: Office Action dated Dec. 26, 2008.
U.S. Appl. No. 11/077,693, filed Mar. 10, 2005, issued as U.S. Pat. No. 7,713,574 on May 11, 2010: Office Action dated Sep. 4, 2009.
U.S. Appl. No. 11/077,713, filed Mar. 10, 2005: Office Action dated Sep. 2, 2009.
U.S. Appl. No. 11/077,713, filed Mar. 10, 2005: Office Action dated Feb. 10, 2009.
U.S. Appl. No. 11/077,713, filed Mar. 10, 2005: Office Action dated Jan. 20, 2010.
U.S. Appl. No. 11/077,713, filed Mar. 10, 2005: Office Action dated May 5, 2008.
U.S. Appl. No. 11/077,714, filed Mar. 10, 2005, issued as U.S. Pat. No. 7,885,697 on Feb. 8, 2011: Office Action dated Jan. 10, 2008.
U.S. Appl. No. 11/280,672, filed Nov. 16, 2005, issued as U.S. Pat. No. 8,050,731 on Nov. 1, 2011: Office Action dated Dec. 10, 2008.
U.S. Appl. No. 11/280,672, filed Nov. 16, 2005, issued as U.S. Pat. No. 8,050,731 on Nov. 1, 2011: Office Action dated Jun. 2, 2009.
U.S. Appl. No. 11/280,672, filed Nov. 16, 2005, issued as U.S. Pat. No. 8,050,731 on Nov. 1, 2011: Office Action dated Oct. 29, 2009.
U.S. Appl. No. 11/280,672, filed Nov. 16, 2005, issued as U.S. Pat. No. 8,050,731 on Nov. 1, 2011: Office Action dated Mar. 11, 2010.
U.S. Appl. No. 11/360,262, filed Feb. 22, 2006, issued as U.S. Pat. No. 8,615,282 on Dec. 24, 2013: Office Action dated Jun. 22, 2009.
U.S. Appl. No. 11/360,262, filed Feb. 22, 2006, issued as U.S. Pat. No. 8,615,282 on Dec. 24, 2013: Office Action dated Apr. 14, 2010.
U.S. Appl. No. 11/404,417, filed Apr. 14, 2006, issued as U.S. Pat. No. 7,613,491 on Nov. 3, 2009: Office Action dated Jan. 23, 2009.
U.S. Appl. No. 11/404,418, filed Apr. 14, 2006, now abandoned: Office Action dated Jul. 23, 2009.
U.S. Appl. No. 11/404,418, filed Apr. 14, 2006, now abandoned: Office Action dated Jan. 29, 2010.
U.S. Appl. No. 11/411,656, filed Apr. 26, 2006, now abandoned: Office Action dated Jul. 26, 2007.
U.S. Appl. No. 11/675,063, filed Feb. 14, 2007, issued as U.S. Nov. 9, 2010: Office Action dated Dec. 3, 2008.
U.S. Appl. No. 11/675,063, filed Feb. 14, 2007, issued as U.S. Nov. 9, 2010: Office Action dated Jun. 10, 2009.
U.S. Appl. No. 11/675,063, filed Feb. 14, 2007, issued as U.S. Nov. 9, 2010: Office Action dated Feb. 19, 2010.
U.S. Appl. No. 11/692,154, filed Mar. 27, 2007, issued as U.S. Pat. No. 7,761,130 on Jul. 20, 2010: Office Action dated Jan. 22, 2009.
U.S. Appl. No. 11/692,154, filed Mar. 27, 2007, issued as U.S. Pat. No. 7,761,130 on Jul. 20, 2010: Office Action dated Jul. 8, 2009.
U.S. Appl. No. 11/335,879, filed Jan. 18, 2006, issued as U.S. Pat. No. 7,651,596 on Jan. 26, 2010: Office Action dated Jun. 26, 2008.
U.S. Appl. No. 11/335,879, filed Jan. 18, 2006, issued as U.S. Pat. No. 7,651,596 on Jan. 26, 2010: Office Action dated Jan. 13, 2009.
U.S. Appl. No. 11/335,879, filed Jan. 18, 2006, issued as U.S. Pat. No. 7,651,596 on Jan. 26, 2010: Office Action dated Jun. 16, 2009.
U.S. Appl. No. 12/139,305, filed Jun. 13, 2008, issued as U.S. Pat. No. RE43399 on May 22, 2012: Office Action dated Jan. 13, 2010.

\* cited by examiner

CELLULOSIC-BASED RESISTANCE DOMAIN FOR AN ANALYTE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a divisional of U.S. application Ser. No. 11/413,238 filed Apr. 28, 2006, which claims the benefit of U.S. Provisional Application No. 60/678,373, filed May 5, 2005. Each of the aforementioned applications is incorporated by reference herein in its entirety, and each is hereby expressly made a part of this specification.

FIELD OF THE INVENTION

The present invention relates generally to systems and methods for measuring an analyte in a host.

BACKGROUND OF THE INVENTION

A variety of sensors are known that use an electrochemical cell to provide output signals by which the presence or absence of an analyte in a sample can be determined. For example in an electrochemical cell, an analyte (or a species derived from it) that is electro-active generates a detectable signal at an electrode, and this signal can be used to detect or measure the presence and/or amount within a biological sample. In some conventional sensors, an enzyme is provided that reacts with the analyte to be measured, and the byproduct of the reaction is qualified or quantified at the electrode. An enzyme has the advantage that it can be very specific to an analyte and also, when the analyte itself is not sufficiently electro-active, can be used to interact with the analyte to generate another species which is electro-active and to which the sensor can produce a desired output. In one conventional amperometric glucose oxidase-based glucose sensor, immobilized glucose oxidase catalyses the oxidation of glucose to form hydrogen peroxide, which is then quantified by amperometric measurement (for example, change in electrical current) through a polarized electrode.

There exists a molar excess of glucose relative to the amount of oxygen in the body; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

Some prior art membrane systems have been disclosed, for example, hydrophobic and hydrophilic urethanes, that allow for the modulation of relative diffusion rates of oxygen and glucose. However many prior art membrane systems have suffered from complex chemical processing issues, such as, controlled heating, long cure times, issues with solvents in depositions techniques, and the like.

SUMMARY OF THE INVENTION

A membrane system is needed that modulates oxygen and glucose (or other analyte) diffusion rates and does not have complex chemical mixing or difficult application processes. The membrane systems of preferred embodiments offer such advantages.

Accordingly, in a first aspect, an analyte sensor for measuring a concentration of an analyte in a host is provided, the sensor comprising an electroactive surface and a membrane system disposed thereon, wherein the membrane system comprises a macromolecular resistance domain configured to control a flux of the analyte therethrough, and wherein the macromolecular resistance domain comprises at least one hydrophilic moiety and at least one hydrophobic moiety.

In an embodiment of the first aspect, the hydrophobic moiety is selected from the group consisting of acetyl, butyryl, propionyl, methoxy, ethoxy, and propoxy.

In an embodiment of the first aspect, the macromolecular resistance domain comprises less than about 35 wt. % acetyl.

In an embodiment of the first aspect, the hydrophilic moiety is selected from the group consisting of hydroxyl, carboxymethyl, and carboxyethyl.

In an embodiment of the first aspect, the macromolecular resistance domain comprises at least about 7 wt. % hydroxyl.

In an embodiment of the first aspect, the sensor is configured to measure a concentration of glucose.

In an embodiment of the first aspect, the sensor is a needle sensor configured for transcutaneous insertion into the host.

In an embodiment of the first aspect, the sensor is configured for wholly implanting into the host.

In an embodiment of the first aspect, the sensor is configured for implantation into a host tissue and wherein the resistance domain is configured to interface with the host tissue.

In an embodiment of the first aspect, the resistance domain is a bioprotective barrier configured to protect the sensor from cellular invasion.

In an embodiment of the first aspect, the membrane system is an ionizing radiation-treated membrane system.

In a second aspect, an analyte sensor for measuring an analyte in a host is provided, the sensor comprising an electroactive surface and a membrane system disposed thereon, wherein the membrane system comprises a resistance domain configured to control a flux of the analyte therethrough, and wherein the resistance domain incorporates hydrophilic substituents and hydrophobic substituents to form a macromolecular structure.

In an embodiment of the second aspect, the hydrophobic substituent is selected from the group consisting of acetyl, butyryl, propionyl, methoxy, ethoxy, and propoxy.

In an embodiment of the second aspect, the macromolecular resistance domain comprises less than about 35 wt. % acetyl.

In an embodiment of the second aspect, the hydrophilic substituent is selected from the group consisting of hydroxyl, carboxymethyl, and carboxyethyl In an embodiment of the second aspect, the macromolecular resistance domain comprises at least about 7 wt. % hydroxyl.

In an embodiment of the second aspect, the sensor is configured to measure glucose.

In an embodiment of the second aspect, the sensor is a needle sensor configured for transcutaneous insertion into the host.

In an embodiment of the second aspect, the sensor is configured for wholly implanting into the host.

In an embodiment of the second aspect, the sensor is configured for implantation into a host tissue and wherein the resistance domain is configured to interface with the host tissue.

In an embodiment of the second aspect, the resistance domain is a bioprotective barrier configured to protect the sensor from cellular invasion.

In an embodiment of the second aspect, the membrane system is an ionizing radiation-treated membrane system.

In a third aspect, a method for forming an analyte sensor for measuring an analyte in a host is provided, the method comprising forming a membrane system on an electroactive surface, wherein the membrane system comprises a resistance domain configured to control a flux of the analyte therethrough, wherein the resistance domain is formed by applying a solution comprising at least one hydrophilic-hydrophobic macromolecule in a solvent system to the electroactive surface.

In an embodiment of the third aspect, the membrane system is formed on the electroactive surface using a deposition technique selected from the group consisting of dip coating, spray coating, spin coating, and casting.

In an embodiment of the third aspect, the resistance domain is formed by dip coating.

In an embodiment of the third aspect, the method further comprises the step of curing the resistance domain for at least about 2 minutes at ambient temperature.

In an embodiment of the third aspect, the resistance domain is formed by dip coating an insertion rate of about 40 inches per minute.

In an embodiment of the third aspect, the resistance domain is formed by dip coating at a dwell time of less than about 1 second.

In an embodiment of the third aspect, the resistance domain is formed by dip coating at a withdrawal rate of about 40 inches per minute.

In an embodiment of the third aspect, the membrane system further comprises an enzyme domain comprising a co-reactant, wherein the co-reactant is capable of undergoing a reaction with the analyte, and wherein the enzyme domain is formed prior to formation of the resistance domain.

In an embodiment of the third aspect, the macromolecule comprises a cellulosic polymer.

In an embodiment of the third aspect, the cellulosic polymer comprises cellulose acetate.

In an embodiment of the third aspect, the cellulosic polymer comprises from about 3 wt. % to about 10 wt. % cellulose acetate.

In an embodiment of the third aspect, the cellulosic polymer comprises about 7 wt. % cellulose acetate.

In a fourth aspect, a method for providing an analyte sensor having a membrane configured to control a flux of an analyte therethrough to an electroactive surface is provided, the method comprising selecting a first hydrophilic-hydrophobic macromolecule having a first hydrophilic content; forming a first membrane system on an electroactive surface, wherein the membrane system comprises a resistance domain configured to control the flux of the analyte therethrough, and wherein the resistance domain is formed from the first hydrophilic-hydrophobic macromolecule; measuring a resistivity of the first membrane system on the electrochemical surface; selecting a second hydrophilic-hydrophobic macromolecule having a second hydrophilic content, wherein the selection is based on the measured resistivity of the first membrane system; and forming a second membrane system on a second electroactive surface, wherein the membrane system comprises a resistance domain configured to control the flux of the analyte therethrough, and wherein the resistance domain is formed from the second hydrophilic-hydrophobic macromolecule, whereby an analyte sensor comprising the second membrane system and the second electroactive surface is obtained.

In an embodiment of the fourth aspect, the second hydrophilic content is higher than the first hydrophilic content and wherein the second membrane system is less resistive to the analyte than the first membrane system.

In an embodiment of the fourth aspect, the second hydrophilic content is lower than the first hydrophilic content and wherein the second membrane system is more resistive to passage therethrough of the analyte than the first membrane system.

In an embodiment of the fourth aspect, a sensitivity of the first membrane system on the electroactive surface is from about 2.5 pA/mg/dL to about 25 pA/mg/dL.

In an embodiment of the fourth aspect, a sensitivity of the second membrane system on the electroactive surface is from about 2.5 pA/mg/dL to about 25 pA/mg/dL.

In a fifth aspect, an electrochemical analyte sensor for measuring a concentration of an analyte in a host is provided, the sensor comprising an electroactive surface and a membrane system disposed thereon, wherein the membrane system comprises an interference domain configured to resist passage therethrough of at least one interfering species, an enzyme domain configured to catalyze a reaction of the analyte with a co-reactant, and a resistance domain configured to control a flux of the analyte therethrough, wherein the resistance domain comprises a cellulosic polymer.

In an embodiment of the fifth aspect, the interference domain is adjacent to the electroactive surface.

In an embodiment of the fifth aspect, the enzyme domain is more distal to the electroactive surface than the interference domain.

In an embodiment of the fifth aspect, the interference domain is more distal to the electroactive surface than the resistance domain.

In an embodiment of the fifth aspect, the interference domain is more distal to the electroactive surface than the enzyme domain.

In an embodiment of the fifth aspect, the resistance domain is more distal to the electroactive surface than the enzyme domain.

In an embodiment of the fifth aspect, the sensor further comprises an electrode domain, wherein the electrode domain is situated between the interference domain and the electroactive surface.

In an embodiment of the fifth aspect, the resistance domain is an ionizing radiation-treated resistance domain, wherein the ionizing radiation is selected from the group consisting of UV, electron beam, gamma, and X-ray radiation.

In an embodiment of the fifth aspect, the cellulosic polymer is selected from the group consisting of cellulose acetate, 2-hydroxyethyl cellulose, cellulose acetate phthalate, cellulose acetate propionate, cellulose acetate butyrate, and cellulose acetate trimellitate.

In an embodiment of the fifth aspect, the cellulosic polymer comprises cellulose acetate.

In an embodiment of the fifth aspect, the cellulose acetate has a molecular weight of less than about 50,000.

In an embodiment of the fifth aspect, the molecular weight of the cellulose acetate is about 38,000.

In an embodiment of the fifth aspect, the cellulose acetate comprises at least about 7 wt. % hydroxyl.

In an embodiment of the fifth aspect, the cellulose acetate comprises about 8.7 wt. % hydroxyl.

In an embodiment of the fifth aspect, the cellulose acetate comprises less than about 35 wt. % acetyl.

In an embodiment of the fifth aspect, the cellulose acetate comprises about 32 wt. % acetyl.

In an embodiment of the fifth aspect, a thickness of the resistance domain is from about 0.05 microns to about 5 microns.

In an embodiment of the fifth aspect, a thickness of the resistance domain is from about 1 to about 3 microns.

In an embodiment of the fifth aspect, the sensor is configured to measure a concentration of glucose.

In an embodiment of the fifth aspect, the sensor is a needle sensor configured for transcutaneous insertion into the host.

In an embodiment of the fifth aspect, the sensor is configured for wholly implanting into the host.

In an embodiment of the fifth aspect, the sensor is configured for implantation into a host tissue and wherein the resistance domain is configured to interface with the host tissue.

In an embodiment of the fifth aspect, the resistance domain is a bioprotective barrier configured to protect the sensor from cellular invasion.

In an embodiment of the fifth aspect, the membrane system is an ionizing radiation-treated membrane system.

In an embodiment of the fifth aspect, the sensor is an ionizing radiation-treated sensor.

In a sixth aspect, an electrochemical analyte sensor for measuring an analyte in a host is provided, the sensor comprising an electroactive surface and a membrane system disposed thereon, wherein the membrane system comprises a resistance domain configured to control a flux of an analyte therethrough, wherein the resistance domain comprises cellulose acetate comprising at least about 7 wt. % hydroxyl.

In an embodiment of the sixth aspect, the cellulose acetate comprises about 8.7 wt. % hydroxyl.

In an embodiment of the sixth aspect, the resistance domain is an ionizing radiation-treated resistance domain, wherein the ionizing radiation is selected from the group consisting of UV, electron beam, gamma, and X-ray radiation.

In an embodiment of the sixth aspect, the cellulose acetate has a molecular weight of less than about 50,000.

In an embodiment of the sixth aspect, a molecular weight of the cellulose acetate is about 38,000.

In an embodiment of the sixth aspect, the cellulose acetate comprises less than about 35 wt. % acetyl.

In an embodiment of the sixth aspect, the cellulose acetate comprises about 32 wt. % acetyl.

In an embodiment of the sixth aspect, a thickness of the resistance domain is from about 0.05 microns to about 5 microns.

In an embodiment of the sixth aspect, a thickness of the resistance domain is from about 1 to about 3 microns.

In an embodiment of the sixth aspect, the membrane system further comprises an enzyme domain configured to catalyze a reaction with the analyte and a co-reactant.

In an embodiment of the sixth aspect, the enzyme domain comprises glucose oxidase.

In an embodiment of the sixth aspect, the membrane system further comprises an interference domain configured to resist passage therethrough of at least one interfering species.

In an embodiment of the sixth aspect, the electroactive surface comprises a working electrode surface and a reference electrode surface, and wherein the interference domain is adjacent to the working reference electrode surface and the reference electrode surface.

In an embodiment of the sixth aspect, the membrane system further comprises an electrode domain.

In an embodiment of the sixth aspect, the sensor is configured to measure a concentration of glucose.

In an embodiment of the sixth aspect, the sensor is a needle sensor configured for transcutaneous insertion into the host.

In an embodiment of the sixth aspect, the sensor is configured for wholly implanting into the host.

In an embodiment of the sixth aspect, the sensor is configured for implantation into a host tissue and wherein the resistance domain is configured to interface with the host tissue.

In an embodiment of the sixth aspect, the resistance domain is a bioprotective barrier configured to protect the sensor from cellular invasion.

In an embodiment of the sixth aspect, the membrane system is a variable frequency microwave-sterilized membrane system.

In an embodiment of the sixth aspect, the membrane system is an ionizing radiation-treated membrane system.

In an embodiment of the sixth aspect, the sensor is an ionizing radiation-sterilized sensor.

In a seventh aspect, an electrochemical analyte sensor for measuring an analyte in a host is provided, the sensor comprising an electroactive surface and a membrane system disposed thereon, wherein the membrane system comprises a resistance domain configured to control a flux of an analyte therethrough, wherein the resistance domain comprises cellulose acetate comprising less than about 35 wt. % acetyl.

In an embodiment of the seventh aspect, the cellulose acetate comprises about 32 wt. % acetyl.

In an embodiment of the seventh aspect, the resistance domain is an ionizing radiation-treated resistance domain, wherein the ionizing radiation is selected from the group consisting of UV, electron beam, gamma, and X-ray radiation.

In an embodiment of the seventh aspect, the cellulose acetate has a molecular weight of less than about 50,000.

In an embodiment of the seventh aspect, a molecular weight of the cellulose acetate is about 38,000.

In an embodiment of the seventh aspect, the cellulose acetate comprises at least about 7 wt. % hydroxyl.

In an embodiment of the seventh aspect, the cellulose acetate comprises about 8.7 wt. % hydroxyl.

In an embodiment of the seventh aspect, a thickness of the resistance domain is from about 0.05 microns to about 5 microns.

In an embodiment of the seventh aspect, a thickness of the resistance domain is from about 1 to about 3 microns.

In an embodiment of the seventh aspect, the membrane system further comprises an enzyme domain configured to catalyze a reaction with the analyte and a co-reactant.

In an embodiment of the seventh aspect, the enzyme domain comprises glucose oxidase.

In an embodiment of the seventh aspect, the membrane system further comprises an interference domain configured to resist passage therethrough of at least one interfering species.

In an embodiment of the seventh aspect, the electroactive surface comprises a working electrode surface and a reference electrode surface, and wherein the interference domain is adjacent to the working reference electrode surface and the reference electrode surface.

In an embodiment of the seventh aspect, the membrane system further comprises an electrode domain.

In an embodiment of the seventh aspect, the sensor is configured to measure a concentration of glucose.

In an embodiment of the seventh aspect, the sensor is a needle sensor configured for transcutaneous insertion into the host.

In an embodiment of the seventh aspect, the sensor is configured for wholly implanting into the host.

In an embodiment of the seventh aspect, the sensor is configured for implantation into a host tissue and wherein the resistance domain is configured to interface with the host tissue.

In an embodiment of the seventh aspect, the resistance domain is a bioprotective barrier configured to protect the sensor from cellular invasion.

In an embodiment of the seventh aspect, the membrane system is an ionizing radiation-treated membrane system.

In an embodiment of the seventh aspect, the sensor is an ionizing radiation-sterilized sensor.

DETAILED DESCRIPTION OF THE PREFERRED EMBODIMENT

Definitions

Figure 1B:
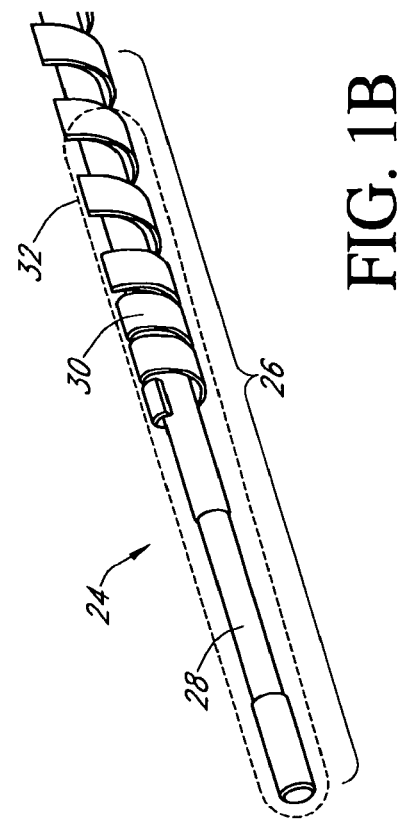
FIG. 1B is an expanded view of an alternative embodiment of a continuous analyte sensor, illustrating the in vivo portion of the sensor.

In order to facilitate an understanding of the preferred embodiments, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (a metabolite of cocaine); biotimidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidum, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and histamine.

The term "host" as used herein is a broad term, and is to be given its ordinary and customary meaning to a person of ordinary skill in the art (and is not to be limited to a special or customized meaning), and refers without limitation to mammals, particularly humans.

The term "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (regularly or irregularly) performed, for example, about every 5 to 10 minutes.

The term "substantial" and "substantially" as used herein are broad terms, and are to be given their ordinary and customary meaning to a person of ordinary skill in the art (and are not to be limited to a special or customized meaning), and refer without limitation to a sufficient amount that provides a desired function. For example, the interference domain of the preferred embodiments is configured to resist a sufficient amount of interfering species such that tracking of glucose levels can be achieved, which may include an amount greater than 50 percent, an amount greater than 60 percent, an amount greater than 70 percent, an amount greater than 80 percent, and an amount greater than 90 percent of interfering species.

The term "domain" as used herein is a broad term, and is to be given its ordinary and customary meaning to a person of ordinary skill in the art (and is not to be limited to a special or customized meaning), and refers without limitation to a region of the membrane system that can be a layer, multiple layers, a uniform or non-uniform gradient (for example, an anisotropic region of a membrane), or a portion of a membrane.

The phrase "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively far from the reference point than another element.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. In general, the term indicates an element is located relatively near to the reference point than another element.

The term "in vivo portion" as used herein is a broad term, and is to be given its ordinary and customary meaning to a person of ordinary skill in the art (and is not to be limited to a special or customized meaning), and refers without limitation to the portion of the device (for example, a sensor) adapted for insertion into and/or existence within a living body of a host.

The term "ex vivo portion" as used herein is a broad term, and is to be given its ordinary and customary meaning to a person of ordinary skill in the art (and is not to be limited to a special or customized meaning), and refers without limitation to the portion of the device (for example, a sensor) adapted to remain and/or exist outside of a living body of a host.

The terms "cellulosic polymers" and "cellulosic polymers" as used herein are broad terms, and are to be given their ordinary and customary meaning to a person of ordinary skill in the art (and are not to be limited to a special or customized meaning), and refer without limitation to derivatives of cellulose with carboxylic acid anhydride(s) therein. Examples of cellulosic polymers include cellulose acetate, 2-hydroxyethyl cellulose, cellulose acetate phthalate, cellulose acetate propionate, cellulose acetate butyrate, cellulose acetate trimellitate, and the like.

The term "cellulose acetate" as used herein is a broad term, and is to be given its ordinary and customary meaning to a person of ordinary skill in the art (and is not to be limited to a special or customized meaning), and refers without limitation to any of several compounds obtained by treating cellulose with acetic anhydride.

The term "cellulose acetate butyrate" as used herein is a broad term, and is to be given its ordinary and customary meaning to a person of ordinary skill in the art (and is not to be limited to a special or customized meaning), and refers without limitation to any of several compounds obtained by treating cellulose with acetic anhydride and butyric anhydride.

The term "Nafion®" as used herein is a broad term, and is to be given its ordinary and customary meaning to a person of ordinary skill in the art (and is not to be limited to a special or customized meaning), and refers without limitation to DuPont's trademark of a sulfonated tetrafluorethylene polymer modified from Teflon® developed in the late 1960s. In general, Nafion® is a perfluorinated polymer that contains small proportions of sulfonic or carboxylic ionic functional groups.

The term "cross link" and "cross linking" as used herein are broad terms, and are to be given their ordinary and customary meaning to a person of ordinary skill in the art (and are not to be limited to a special or customized meaning), and refer without limitation to joining (adjacent chains of a polymer or protein) by creating covalent bonds. Cross linking can be accomplished by techniques such as thermal reaction, chemical reaction or by providing ionizing radiation (for example, electron beam radiation, UV radiation, or gamma radiation). In preferred embodiments, cross linking utilizes a technique that forms free radicals, for example, electron beam exposure.

The term "ionizing radiation" as used herein is a broad term, and is to be given its ordinary and customary meaning to a person of ordinary skill in the art (and is not to be limited to a special or customized meaning), and refers without limitation to radiation consisting of particles, X-ray beams, electron beams, UV beams, or gamma ray beams, which produce ions in the medium through which it passes.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The term "membrane system," as used herein is a broad term, and is to be given its ordinary and customary meaning to a person of ordinary skill in the art (and is not to be limited to a special or customized meaning), and refers without limitation to a permeable or semi-permeable membrane that can be comprised of one or more domains and is typically constructed of materials of a few microns thickness or more, which is permeable to oxygen and is optionally permeable to, e.g., glucose or another analyte. In one example, the membrane system comprises an immobilized glucose oxidase enzyme, which enables a reaction to occur between glucose and oxygen whereby a concentration of glucose can be measured.

The term "sensor" as used herein is a broad term, and is to be given its ordinary and customary meaning to a person of ordinary skill in the art (and is not to be limited to a special or customized meaning), and refers without limitation to the component or region of a device by which an analyte can be quantified.

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

The term "casting" as used herein is a broad term, and is to be given its ordinary and customary meaning to a person of ordinary skill in the art (and is not to be limited to a special or customized meaning), and refers without limitation to a process where a fluid material is applied to a surface or surfaces and allowed to cure or dry. The term is broad enough to encompass a variety of coating techniques, for example, using a draw-down machine (i.e., drawing-down), dip coating, spray coating, spin coating, tampo printing, or the like.

The term "dip coating" as used herein is a broad term, and is to be given its ordinary and customary meaning to a person of ordinary skill in the art (and is not to be limited to a special or customized meaning), and refers without limitation to coating which involves dipping an object or material into a liquid coating substance.

The term "spray coating" as used herein is a broad term, and is to be given its ordinary and customary meaning to a person of ordinary skill in the art (and is not to be limited to a special or customized meaning), and refers without limitation to coating which involves spraying a liquid coating substance onto an object or material.

The term "spin coating" as used herein is a broad term, and is to be given its ordinary and customary meaning to a person of ordinary skill in the art (and is not to be limited to a special or customized meaning), and refers without limitation to a coating process in which a thin film is created by dropping a raw material solution onto a substrate while it is rotating.

The terms "solvent" and "solvent systems" as used herein are broad terms, and are to be given their ordinary and customary meaning to a person of ordinary skill in the art (and are not to be limited to a special or customized meaning), and refer without limitation to substances (e.g., liquids) capable of dissolving or dispersing one or more other substances. Solvents and solvent systems can include compounds and/or solutions that include components in addition to the solvent itself.

The term "hydrophobic" as used herein is a broad term, and is to be given its ordinary and customary meaning to a person of ordinary skill in the art (and is not to be limited to a special or customized meaning), and refers without limitation to a substance that is only weakly attracted to water. In the context of the preferred embodiments, the term hydrophobic is relative to other substituents or moieties in a particular membrane or domain. For example, a substituent or moiety is hydrophobic if it is more hydrophobic than the other (e.g., hydrophilic) substituent or moiety.

The term "hydrophilic" as used herein is a broad term, and is to be given its ordinary and customary meaning to a person of ordinary skill in the art (and is not to be limited to a special or customized meaning), and refers without limitation to a substance that is strongly attracted to water. In the context of the preferred embodiments, the term hydrophilic is relative to other substituents or moieties in a particular membrane or domain. For example, a substituent or moiety is hydrophilic if it is more hydrophilic than the other (e.g., hydrophobic) substituent or moiety.

The term "macromolecule" as used herein is a broad term, and is to be given its ordinary and customary meaning to a person of ordinary skill in the art (and is not to be limited to a special or customized meaning), and refers without limitation to a molecule of high relative molecular mass, the structure of which essentially comprises the multiple repetition of a number of constitutional units.

The term "moiety" as used herein is a broad term, and is to be given its ordinary and customary meaning to a person of ordinary skill in the art (and is not to be limited to a special or customized meaning), and refers without limitation to a part of a molecule.

The term "substituent" as used herein is a broad term, and is to be given its ordinary and customary meaning to a person of ordinary skill in the art (and is not to be limited to a special or customized meaning), and refers without limitation to an atom or group of atoms that replaces another atom or group in a molecule (or macromolecule).

The terms "sensitivity" and "slope" as used herein are broad terms, and are to be given their ordinary and customary meaning to a person of ordinary skill in the art (and are not to be limited to a special or customized meaning), and refer without limitation to an amount of electrical current produced by a predetermined amount (unit) of the measured analyte. For example, in one preferred embodiment, a sensor has a sensitivity (or slope) of about 3.5 to about 7.5 picoAmps of current for every 1 mg/dL of glucose analyte.

Analyte Sensor

The preferred embodiments relate to the use of an analyte sensor that measures a concentration of analyte of interest or a substance indicative of the concentration or presence of the analyte. In some embodiments, the sensor is a continuous device, for example a subcutaneous, transdermal (e.g., transcutaneous), or intravascular device. In some embodiments, the device can analyze a plurality of intermittent blood samples. The analyte sensor can use any method of analyte-sensing, including enzymatic, chemical, physical, electrochemical, spectrophotometric, polarimetric, calorimetric, radiometric, or the like.

The analyte sensor uses any method, including invasive, minimally invasive, and non-invasive sensing techniques, to provide an output signal indicative of the concentration of the analyte of interest. The output signal is typically a raw signal that is used to provide a useful value of the analyte of interest to a user, such as a patient or physician, who can be using the device. Accordingly, appropriate smoothing, calibration, and evaluation methods can be applied to the raw signal and/or system as a whole to provide relevant and acceptable estimated analyte data to the user.

The methods and devices of preferred embodiments can be employed in a continuous glucose sensor that measures a concentration of glucose or a substance indicative of a concentration or a presence of glucose. However, certain methods and devices of preferred embodiments are also suitable for use in connection with non-continuous (e.g., single point measurement or finger stick) monitors, such as the OneTouch® system manufactured by LifeScan, Inc., or monitors as disclosed in U.S. Pat. Nos. 5,418,142; 5,515,170; 5,526,120; 5,922,530; 5,968,836; and 6,335,203. In some embodiments, the glucose sensor is an invasive, minimally-invasive, or non-invasive device, for example a subcutaneous, transdermal, or intravascular device. In some embodiments, the device can analyze a plurality of intermittent biological samples, such as blood, interstitial fluid, or the like. The glucose sensor can use any method of glucose-measurement, including colorimetric, enzymatic, chemical, physical, electrochemical, spectrophotometric, polarimetric, calorimetric, radiometric, or the like. In alternative embodiments, the sensor can be any sensor capable of determining the level of an analyte in the body, for example oxygen, lactase, hormones, cholesterol, medicaments, viruses, or the like.

The glucose sensor uses any method to provide an output signal indicative of the concentration of the glucose. The output signal is typically a raw data stream that is used to provide a value indicative of the measured glucose concentration to a patient or doctor, for example.

One exemplary embodiment described in detail below utilizes an implantable glucose sensor. Another exemplary embodiment described in detail below utilizes a transcutaneous glucose sensor.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference.

Although a few exemplary embodiments of continuous glucose sensors are illustrated and described herein, it should be understood that the disclosed embodiments are applicable to any device capable of single analyte, substantially continual or substantially continuous measurement of a concentration of analyte of interest and providing an output signal that represents the concentration of that analyte.

Figure 1A:
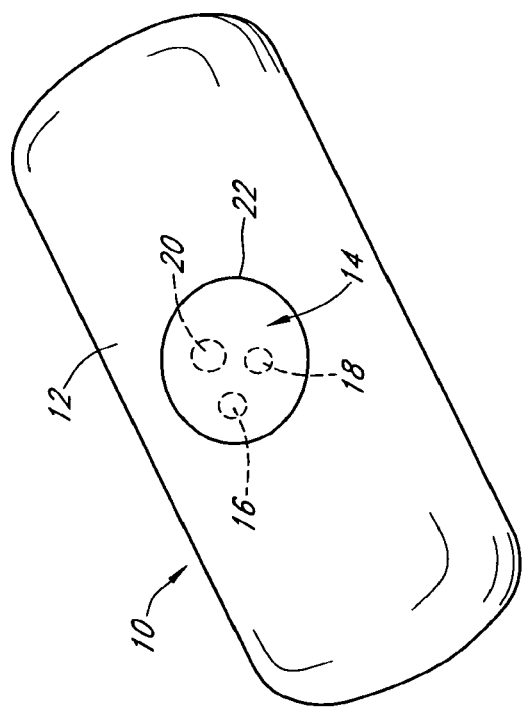
FIG. 1A is a perspective view of a continuous analyte sensor, including an implantable body with a membrane system disposed thereon

FIG. 1A is a perspective view of an analyte sensor in one embodiment, including an implantable body with a sensing region including a membrane system disposed thereon. In the illustrated embodiment, the analyte sensor 10 includes a body 12 and a sensing region 14 including membrane and electrode systems configured to measure the analyte. Preferably, the sensor 10 is wholly implanted into the subcutaneous tissue of a host, such as described in U.S. Publ. No. US-2006-0015020 A1; U.S. Publ. No. US-2005-0245799-A1; U.S. Publ. No. US-2005-0192557-A1; U.S. Publ. No. US-2004-0199059 A1; U.S. Publ. No. US-2005-0027463-A1; and U.S. Pat. No. 6,001,067.

The body 12 of the sensor 10 can be formed from a variety of materials, including metals, ceramics, plastics, or composites thereof. In one embodiment, the sensor is formed from thermoset molded around the sensor electronics. U.S. Publ. No. US-2004-0199059 A1 discloses suitable configurations for the body.

In some embodiments, the sensing region 14 includes a working electrode 16 a reference electrode 18, and a counter electrode 20, which are shown in phantom under membrane system 22. Membrane system 22 is preferably deposited over the electroactive surfaces of the electrodes (16, 18, 20) and includes a plurality of domains or layers, such as described in more detail below, with reference to FIGS. 2A and 2B. In general, the membrane system 22 may be disposed over (deposited on) the electroactive surfaces using methods appreciated by one skilled in the art. See, for example, U.S. Publ. No. US-2006-0015020-A1.

The sensing region 14 comprises electroactive surfaces (the exposed surfaces of electrodes 16, 18, 20), which are in contact with an electrolyte phase (not shown), which is a free-flowing fluid phase disposed between the membrane system 22 and the electroactive surfaces. In this embodiment, the counter electrode 20 is provided to balance the current generated by the species being measured at the working electrode. In the case of glucose oxidase based analyte sensors, the species being measured at the working electrode is $H_2O_2$. Glucose oxidase catalyzes the conversion of oxygen and glucose to hydrogen peroxide and gluconate according to the following reaction:

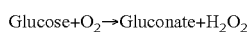

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of the working electrode and produces two protons (2H$^+$), two electrons (2e$^-$), and one oxygen molecule (O$_2$). Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of H$_2$O$_2$ that diffuses to the working electrodes. The output signal is typically a raw data stream (measured in "counts") that can be used to provide a useful value of the measured analyte concentration in a host to the patient or doctor, for example.

FIG. 1B is an expanded view of an alternative exemplary embodiment of a continuous analyte sensor 24, also referred to as a transcutaneous analyte sensor, or needle-type sensor, particularly illustrating the in vivo portion 26 of the sensor. In this embodiment, the in vivo portion of the sensor is the portion adapted for insertion under the host's skin, while an ex vivo portion of the sensor (not shown) is the portion that remains above the host's skin after sensor insertion and operably connects to an electronics unit. In the illustrated embodiment, the analyte sensor 24, includes two electrodes, i.e., a working electrode 28 and at least one additional electrode 30, which may function as a counter and/or reference electrode, hereinafter referred to as the reference electrode 30. Preferably, each electrode is formed from a fine wire, with a diameter in the range of 0.001 to 0.010 inches, for example, and may be formed from plated wire or bulk material, however the electrodes may be deposited on a substrate or other known configurations as is appreciated by one skilled in the art.

In one embodiment, the working electrode 28 comprises a wire formed from a conductive material, such as platinum, palladium, gold, conductive carbon, conductive polymer, or the like. The working electrode 28 is configured and arranged to measure the concentration of an analyte, e.g., glucose. The working electrode 28 is covered with an insulating material, for example a non-conductive polymer. Dip coating, spray coating, vapor-deposition, or other coating or deposition techniques can be used to deposit the insulating material on the working electrode, for example. In one preferred embodiment, the insulating material comprises Parylene, which can be an advantageous conformal coating for its strength, lubricity, and electrical insulation properties, however, a variety of other insulating materials can be used, for example, fluorinated polymers, polyethyleneterephthalate, polyurethane, polyimide, or the like. Preferably, the reference electrode 30, which may function as a reference electrode alone, or as a dual reference and counter electrode, is formed from silver, silver/silver chloride, or the like.

Preferably, the electrodes are juxtapositioned and/or twisted with or around each other; however other configurations are also possible. In one example, the reference electrode 30 is helically wound around the working electrode 28 as illustrated in FIG. 1B. The assembly of wires may then be optionally coated together with an insulating material, similar to that described above, in order to provide an insulating attachment. Some portion of the coated assembly structure is then stripped to expose the necessary electroactive surfaces. In some alternative embodiments, additional electrodes may be included within the assembly, for example, a three-electrode system (including separate reference and counter electrodes) as is appreciated by one skilled in the art.

Preferably, a membrane system 32 is deposited over the electroactive surfaces of the sensor 24 and includes a plurality of domains or layers, such as described in more detail below, with reference to FIGS. 2A and 2B. The membrane system 32 may be deposited on the exposed electroactive surfaces using known thin film techniques (for example, spraying, vapor deposition, electro-depositing, dipping, tampo printing, or the like).

In the illustrated embodiment, the sensor is an enzyme-based electrochemical sensor, wherein the working electrode 16 measures the hydrogen peroxide produced by the enzyme catalyzed reaction of glucose being detected and creates a measurable electronic current (for example, detection of glucose utilizing glucose oxidase produces H$_2$O$_2$ peroxide as a by-product, H$_2$O$_2$ reacts with the surface of the working electrode producing two protons (2H$^+$), two electrons (2e$^-$) and one molecule of oxygen (O$_2$) which produces the electronic current being detected), such as described in more detail above and as is appreciated by one skilled in the art. Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of H$_2$O$_2$ that diffuses to the working electrodes. The output signal is typically a raw data stream that is used to provide a useful value of the measured analyte concentration in a host to the patient or doctor, for example.

U.S. Publ. No. US-2006-0020187-A1 and U.S. Publ. No. US-2006-0015024-A1 disclose system and methods for a transcutaneous analyte sensor that can be incorporated herein with the preferred embodiments.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, for example. All of the above patents are incorporated in their entirety herein by reference and are not inclusive of all applicable analyte sensors; in general, it should be understood that the disclosed embodiments are applicable to a variety of analyte sensor configurations.

Membrane System

In general, analyte sensors include a membrane system that functions to control the flux of a biological fluid there through and/or to protect sensitive regions of the sensor from contamination by the biological fluid, for example. Some conventional electrochemical enzyme-based analyte sensors generally include a membrane system that controls the flux of the analyte being measured, protects the electrodes from contamination of the biological fluid, and/or provides an enzyme that catalyzes the reaction of the analyte with a co-factor, for example. See, e.g., U.S. Publ. No. US-2005-0245799-A1 and U.S. Publ. No. US-2006-0020187-A1.

The membrane systems of the preferred embodiments can include any membrane configuration suitable for use with any analyte sensor (such as described in more detail above). In general, the membrane systems of the preferred embodiments includes a plurality of domains, all or some of which can be adhered to or deposited on, over, or around the analyte sensor as is appreciated by one skilled in the art. In one embodiment, the membrane system generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface. Accordingly, the membrane systems of the preferred embodiments include a plurality of domains or layers, for example, an interference domain, an enzyme domain, and a resistance domain, and may include additional domains, such as an electrode domain, a cell disruptive domain, a cell impermeable domain, and/or an oxygen domain (not shown), such as described in more detail elsewhere. However, it is understood that a membrane system modified for other sensors, for example, by including fewer or additional domains is within the scope of the preferred embodiments.

In some embodiments, one or more domains of the membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. U.S. Publ. No. US-2005-0245799-A1 describes biointerface and membrane system configurations and materials that may be applied to the preferred embodiments.

Figure 2A:
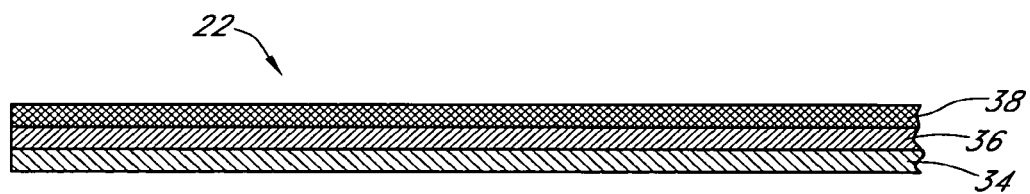
FIG. 2A is a schematic view of a membrane system in one embodiment, configured for deposition over the electroactive surfaces of the analyte sensor of FIG. 1A.
Figure 2B:
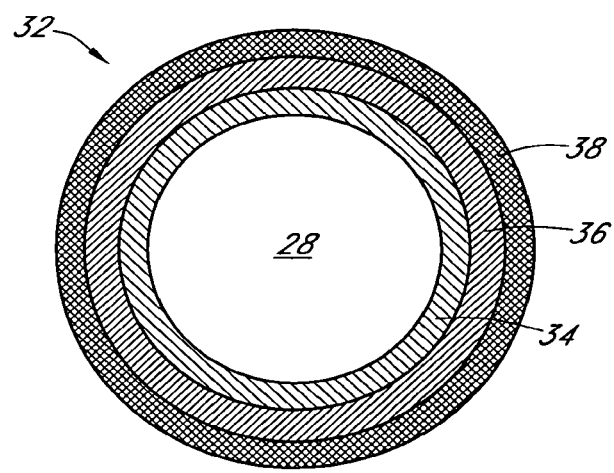
FIG. 2B is a schematic view of a membrane system in an alternative embodiment, configured for deposition over the electroactive surfaces of the analyte sensor of FIG. 1B.

FIGS. 2A and 2B are schematic views membrane systems in some embodiments that may be disposed over the electroactive surfaces of the analyte sensors of FIGS. 1A and 1B, respectively, wherein the membrane system includes at least a resistance domain, such as described in more detail below. In preferred embodiments, the membrane system of the preferred embodiments additionally includes enzyme and interference domains, such as described in more detail below. However, it is understood that the membrane system of the preferred embodiments can be modified for use in other sensors, by including only one or more of the domains, additional domains not recited above, or for other sensor configurations.

For example, the illustrated embodiment (described below) includes the interference domain disposed most proximal (i.e., adjacent) to the exposed electroactive surfaces, which functions both to block interfering species and to provide hydrophilicity to the exposed electroactive surface thereby enabling electrical communication between the working and reference (and/or counter) electrodes. However, in some alternative embodiments, a separate electrode domain can be deposited on the exposed electroactive surface prior to deposition of the interference domain, for example.

Interference Domain

Interferants are molecules or other species that are electro-reduced or electro-oxidized at the electrochemically reactive surfaces, either directly or via an electron transfer agent, to produce a false signal. In preferred embodiments, an interference domain 34 is provided that substantially restricts, resists, or blocks the flow of one or more interfering species. Some known interfering species for a glucose sensor as described in more detail above include acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain of the preferred embodiments is less permeable to one or more of the interfering species than to the analyte.

In one embodiment, the interference domain 34 is formed from one or more cellulosic polymers. In general, cellulosic polymers include polymers such as cellulose acetate, cellulose acetate butyrate, 2-hydroxyethyl cellulose, cellulose acetate phthalate, cellulose acetate propionate, cellulose acetate trimellitate, and the like.

In one preferred embodiment, the interference domain 34 is formed from cellulose acetate. Cellulose acetate with a molecular weight of at least about 30,000 to at least about 100,000, preferably from about 35,000, 40,000, or 45,000 to about 55,000, 60,000, 65,000, 70,000, 75,000, 80,000, 85,000, 90,000, or 95,000, and more preferably about 50,000 is preferred. In certain embodiments, however, higher or lower molecular weights can be preferred. Additionally, a casting solution or dispersion of cellulose acetate at a weight percent of at least about 3% to at least about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 7% is preferred. A hydroxyl content of cellulose acetate is at least about 2.0% is preferred, and more preferably at least about 3.5%. An acetyl content of cellulose acetate is greater than about 38%, and more preferably greater than about 39.7%. It can be desirable to employ a mixture of cellulose acetates with molecular weights in a single solution, or to deposit multiple layers of cellulose acetate from different solutions comprising cellulose acetates of different molecular weights, different concentrations, or different chemistries. It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

In some alternative embodiments, additional polymers, such as Nafion®, can be used in combination with cellulosic polymers to provide equivalent and/or enhanced function of the interference domain. In one such exemplary embodiment, a 5 wt % Nafion® casting solution or dispersion is used in combination with a 7 wt % cellulose acetate casting solution or dispersion, for example by dip coating at least one layer of cellulose acetate and subsequently dip coating at least one layer Nafion® onto a needle-type sensor such as described with reference to FIGS. 1B and 2B. Any number of coatings or layers formed in any order may be suitable for forming the interference domain of the preferred embodiments.

In another preferred embodiment, the interference domain 34 is formed from cellulose acetate butyrate. Cellulose acetate butyrate with a molecular weight of about 10,000 daltons to about 75,000 daltons, preferably from about 15,000, 20,000, or 25,000 daltons to about 50,000, 55,000, 60,000, 65,000, or 70,000 daltons, and more preferably about 20,000 daltons is preferred. In certain embodiments, however, higher or lower molecular weights can be preferred. Additionally, a casting solution or dispersion of cellulose acetate butyrate at a weight percent of about 15% to about 25%, preferably from about 15%, 16%, 17%, 18%, 19% to about 20%, 21%, 22%, 23%, 24% or 25%, and more preferably about 18% is preferred. Preferably, the casting solution includes a solvent or solvent system, for example an acetone:ethanol solvent system. Higher or lower concentrations can be preferred in certain embodiments. A plurality of layers of cellulose acetate butyrate can be advantageously combined to form the interference domain in some embodiments, for example, three layers can be employed. It can be desirable to employ a mixture of cellulose acetate butyrate components with different molecular weights in a single solution, or to deposit multiple layers of cellulose acetate butyrate from different solutions comprising cellulose acetate butyrate of different molecular weights, different concentrations, and/or different chemistries (e.g., functional groups). It can also be desirable to include additional substances in the casting solutions or dispersions, e.g., functionalizing agents, crosslinking agents, other polymeric substances, substances capable of modifying the hydrophilicity/hydrophobicity of the resulting layer, and the like.

Additionally, more than one cellulosic polymer can be used to form the interference domain of the preferred embodiments; for example, cellulose acetate and cellulose acetate butyrate can be used together such as described by U.S. Pat. No. 5,520,788. Numerous prior art references describe the use of cellulose acetate and/or Nafion® to block interfering species in a glucose sensor, some of which are cited and incorporated herein by reference in their entirety, including Wilson et al., Analytical Chemistry, 1994, vol. 66, pp 1183-1188; Matsumoto et al., Sensors and Actuators B, 1998, Vol. 49, pp 68-72; Buck et al., Analytica Chimica Acta, 1996, Vol. 319, pp. 335-345; and U.S. Pat. Nos. 3,979,274, 4,073,713, and 5,520,788.

In some alternative embodiments, polyurethanes, polymers having pendant ionic groups, and polymers having controlled pore size, for example, can be utilized as a base material for the interference domain. In one embodiment, the interference domain includes a thin, hydrophobic membrane that is nonswellable in water and restricts diffusion of low molecular weight species. The interference domain 34 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Publ. No. US-2005-0115832-A1; U.S. Publ. No. US-2005-0176136-A1; U.S. Publ. No. US-2005-0161346-A1; and U.S. Publ. No. US-2005-0143635-A1. In some alternative embodiments, a distinct interference domain is not included.

In general, the formation of the interference domain 34 on a surface requires a solvent in order to dissolve the polymer prior to film formation thereon. In one preferred embodiment, acetone and ethanol are used to dissolve cellulose acetate; however one skilled in the art appreciates numerous solvents that are available for cellulosic polymers (and other polymers). Additionally, one skilled in the art appreciates that the relative amounts of solvent may be dependent upon the cellulosic polymer (or other polymer) used, its molecular weight, its method of deposition, and its desired thickness. However, in preferred embodiments, a percent solute from about 1% to about 10% can be used (to form the interference domain solution) to produce the desired result, namely, the interference domain of the preferred embodiments. In fact, it is understood that the cellulosic polymer (or other polymer) used, its molecular weight, method of deposition, and desired thickness are all parameters that may vary depending on one or more other of the parameters, and can be varied accordingly as is appreciated by one skilled in the art.

In preferred embodiments, the interference domain 34 is deposited onto directly onto the electroactive surfaces of the sensor for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 1, 1.5 or 2 microns to about 2.5 or 3 microns. Thicker membranes can also be useful, but thinner membranes are generally preferred because they have a lower impact on the rate of diffusion of hydrogen peroxide from the enzyme membrane to the electrodes. In some alternative embodiments, a distinct electrode domain is formed directly on the exposed electroactive surfaces prior to deposition of the interference domain as described in more detail with reference to U.S. Publ. No. US-2006-0020187-A1.

In general, the membrane system of the preferred embodiments can be formed and/or deposited on the exposed electroactive surfaces (e.g., at least the working and reference electrodes) using known thin film techniques (for example, casting, spray coating, drawing down, vapor deposition, electro-depositing, dip coating, spin coating, tampo printing, and the like). Preferably, the interference domain 34 is deposited by spray or dip coating. In some embodiments, the interference domain 34 is formed by dip coating one or more times (namely, forming one or more of the same or different layers) in a coating solution(s). In embodiments wherein dip coating is used to deposit the interference domain at room temperature, a preferred insertion rate of from about 0.25 inch per minute to about 100 inches per minute, with a preferred dwell time of from about 0 seconds to about 2 minutes, and a preferred withdrawal rate of from about 0.25 inch per minute to about 100 inches per minute provide a functional coating. Suitable cure time ranges from about 1 minute to about 30 minutes at room temperature (and can be accomplished under vacuum (e.g., 20 to 30 in Hg)). However, values outside of those set forth above can be acceptable or even desirable in certain embodiments, for example, dependent upon viscosity and surface tension as is appreciated by one skilled in the art. In one exemplary embodiment of needle-type (transcutaneous) sensor such as described with reference to FIGS. 1B and 2B, a cellulose acetate interference domain 34 is formed by dip coating the sensor into an interference domain solution using an insertion rate of between about 20 and about 60 inches/min., preferably 40 inches/min., a dwell time of between about 0 and about 5 seconds, preferably 0 seconds, and a withdrawal rate of between about 20 and about 60 inches/min., preferably 40 inches/min., and curing the domain for from about 3 minutes at room temperature. The dip process may be repeated at least one time and up to 10 times or more, preferably about 4 times, to form an appropriate domain thickness (e.g., 1-2 microns). However, the interference domain can be formed using any known method as will be appreciated by one skilled in the art.

Enzyme Domain

In preferred embodiments, the membrane system further includes an enzyme domain 36 disposed more distally from the electroactive surfaces than the interference domain 34, however other configurations are possible (e.g., interference domain may be deposited over enzyme domain). In the preferred embodiments, the enzyme domain 36 provides an enzyme to catalyze the reaction of the analyte and its co-reactant, as described in more detail below. In the preferred embodiments of a glucose sensor, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain 36 is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See U.S. Publ. No. US-2005-0054909-A1.

In preferred embodiments, the enzyme domain 36 is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. However in some embodiments, the enzyme domain is deposited onto an optional electrode domain or directly onto the electroactive surfaces. Preferably, the enzyme domain 36 is deposited by spray or dip coating. In one embodiment of needle-type (transcutaneous) sensor such as described with reference to FIGS. 1B and 2B, the enzyme domain 36 is formed by dip coating the interference domain coated sensor into an enzyme domain solution and curing the domain for from about 15 to about 30 minutes at a temperature of from about 40 to about 55° C. (and can be accomplished under vacuum (e.g., 20 to 30 in Hg)). In embodiments wherein dip coating is used to deposit the enzyme domain at room temperature, a preferred insertion rate of from about 0.25 inch per minute to about 3 inches per minute, with a preferred dwell time of from about 0.5 minutes to about 2 minutes, and a preferred withdrawal rate of from about 0.25 inch per minute to about 2 inches per minute provide a functional coating. However, values outside of those set forth above can be acceptable or even desirable in certain embodiments, for example, dependent upon viscosity and surface tension as is appreciated by one skilled in the art. In one embodiment, the enzyme domain 36 is formed by dip coating two times (namely, forming two layers) in an enzyme domain solution and curing at 50° C. under vacuum for 20 minutes. However, in some embodiments, the enzyme domain can be formed by dip coating and/or spray coating one or more layers at a predetermined concentration of the coating solution, insertion rate, dwell time, withdrawal rate, and/or desired thickness.

Resistance Domain

In preferred embodiments, the membrane system includes a resistance domain 38 disposed more distal from the electroactive surfaces than the enzyme domain 36. Although the following description is directed to a resistance domain for a glucose sensor, the resistance domain can be modified for other analytes and co-reactants as well.

The resistance domain 38 includes a semi permeable membrane that controls the flux of oxygen and glucose to the underlying enzyme domain 36, preferably rendering oxygen in a non-rate-limiting excess. As a result, the upper limit of linearity of glucose measurement is extended to a much higher value than that which is achieved without the resistance domain. In one embodiment, the resistance domain 38 exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In some embodiments, the resistance domain is formed as a macromolecule including at least one hydrophilic moiety and at least one hydrophobic moiety. Some hydrophobic moieties suitable for the resistance domain include acetyl, butyryl, propionyl, methoxy, ethoxy, and propoxy. In one preferred embodiment, the hydrophobic moiety is acetyl; while the preferred macromolecule has less than about 35% acetyl, other concentrations are possible. Some hydrophilic moieties suitable for the resistance domain include hydroxyl, carboxymethyl, and carboxyethyl. In one preferred embodiment, the preferred hydrophilic moiety is hydroxyl; while the preferred macromolecule has more than about 7% hydroxyl, other concentrations are also possible.

In some embodiments, the macromolecule comprises a cellulosic polymer; in one preferred embodiment, the macromolecule comprises cellulose acetate (CA). In one preferred CA resistance domain, the CA resistance domain is formed from CA that has a weight percent of at least about 3% to about 10%, and more preferably about 7%. Suitable thin film deposition techniques and solvents are appreciated by one skilled in the art. In some embodiments, dip coating, spray coating, spin coating, vapor deposition or casting are used to form the membrane domain on a surface (e.g., of the sensor).

A resistance domain formed from a macromolecule as described herein is advantageous because the functionality (e.g., relative resistivity or analyte flux) of the resistance domain can be easily tuned (increased or decreased) by changing the relative amounts of the hydrophobic and hydrophilic moieties or substituents. Namely, macromolecular engineering applied to the resistance domain enables selection and placement of the hydrophilic and hydrophobic moieties onto the same chain (backbone), and thereby forming a resistance domain without special processing or mixing required. In some embodiments, the resistance domain 38 is formed from one or more cellulosic polymers. In general, cellulosic polymers include polymers such as cellulose acetate, cellulose acetate butyrate, 2-hydroxyethyl cellulose, cellulose acetate phthalate, cellulose acetate propionate, cellulose acetate trimellitate, and the like.

In one preferred embodiment, the resistance domain 38 is formed from cellulose acetate. Cellulose acetate with a molecular weight of at least about 30,000 to at least about 100,000, preferably from about 35,000, 40,000, or 45,000 to about 55,000, 60,000, 65,000, 70,000, 75,000, 80,000, 85,000, 90,000, or 95,000, and more preferably about 38,000 is preferred. Additionally, a casting solution or dispersion of cellulose acetate at a weight percent of at least about 3% to at least about 10%, preferably from about 3.5%, 4.0%, 4.5%, 5.0%, 5.5%, 6.0%, or 6.5% to about 7.5%, 8.0%, 8.5%, 9.0%, or 9.5%, and more preferably about 7% is preferred. A hydroxyl content of cellulose acetate is at least about 7% is preferred, and more preferably at least about 8.7%. An acetyl content of cellulose acetate is less than about 35%, and more preferably less than about 32%. In certain embodiments, however, higher or lower molecular weights, acetyl content, and/or hydroxyl content can be preferred. It can be desirable to employ a mixture of cellulose acetates with molecular weights in a single solution, or to deposit multiple layers of cellulose acetate from different solutions comprising cellulose acetates of different molecular weights, different concentrations, or different chemistries. It can also be desirable to include additional substances in the casting solutions or dispersions, e.g., functionalizing agents, crosslinking agents, other polymeric substances, substances capable of modifying the hydrophilicity/hydrophobicity of the resulting layer, and the like. In some embodiments, more than one cellulosic polymer can be used to form the resistance domain of the preferred embodiments; for example, cellulose acetate and cellulose acetate butyrate can be used together.

In general, the cellulosic polymer chosen for the resistance domain of the preferred embodiments can have a hydroxyl content with sufficient hydrophilicity such that glucose permeates through the domain (or membrane system). Additionally, modulating the hydroxyl to acetyl ratio within the cellulosic polymer can be used to modulate the relative permeability of glucose through the resistance domain. For example, it is believed that by increasing the hydroxyl concentration an increased slope (i.e., glucose permeability) can be achieved. The ability to easily and reliably modulate the relative diffusivity of the resistance domain to the analyte (and its co-reactant) is advantageous as is appreciated by one skilled in the art.

In general, the formation of the resistance domain 38 on a surface requires a solvent system in order to dissolve the polymer prior to film formation thereon. In one preferred embodiment, acetone and ethanol are used to dissolve cellulose acetate; however one skilled in the art appreciates numerous solvent systems that are available for cellulosic polymers (and other polymers), for example acetone and water can be used. Additionally, one skilled in the art appreciates that the relative amounts of solvent may be dependent upon the cellulosic polymer (or other polymer) used, its molecular weight, its method of deposition, and its desired thickness. However, in preferred embodiments, a percent solute from about 1% to about 10% can be used (to form the resistance domain solution) to produce the desired result, namely, the resistance domain of the preferred embodiments. In fact, it is understood that the cellulosic based polymer (or other polymer) used, its molecular weight, method of deposition, hydroxyl content, acetyl content, and desired thickness are all parameters that may vary depending on one or more other of the parameters, and can be varied accordingly as is appreciated by one skilled in the art.

In preferred embodiments, the resistance domain 38 is deposited onto the enzyme domain 36 to yield a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Preferably, the resistance domain is deposited onto the enzyme domain by spray coating or dip coating.

In general, the membrane system of the preferred embodiments can be formed and/or deposited on the exposed electroactive surfaces (e.g., at least the working and reference electrodes) using known thin film techniques (for example, casting, spray coating, drawing down, vapor deposition, electro-depositing, dip coating, and the like). Preferably, the resistance domain 38 is deposited by spray or dip coating. In some embodiments, the resistance domain 38 is formed by dip coating one or more times (namely, forming one or more of the same or different layers) in a coating solution(s). In embodiments wherein dip coating is used to deposit the resistance domain at room temperature, a preferred insertion rate of from about 10 inches per minute to about 100 inches per minute, with a preferred dwell time of from about 0 seconds to about 10 seconds, and a preferred withdrawal rate of from about 10 inch per minute to about 100 inches per minute provide a functional coating. Suitable cure time ranges from about 1 minute to about 30 minutes, and more preferably about 3 minutes, at room temperature (and can be accomplished under vacuum (e.g., 20 to 30 in Hg)). However, values outside of those set forth above can be acceptable or even desirable in certain embodiments, for example, dependent upon viscosity and surface tension as is appreciated by one skilled in the art. In one exemplary embodiment of needle-type (transcutaneous) sensor such as described with reference to FIGS. 1B and 2B, the resistance domain 38 is formed by dip coating the sensor into an resistance domain solution using an insertion rate of about 40 inches/min., a dwell time of less than about 1 second, and a withdrawal rate of about 40 inches/min., and curing the domain for from about 3 minutes at room temperature. While not wishing to be bound by theory, it is believed that a fast dip rate as described above advantageously provides the necessary membrane coating while minimizing exposure of the enzyme domain to the solvent used in the resistance domain solution, which has been known to inactivate the enzyme in some prior art sensors. The dip process may be repeated from about 1 to 10 times or more, preferably about 3 times, to form an appropriate domain thickness (e.g., about 1 to about 5 microns). However, the resistance domain can be formed using any known method as will be appreciated by one skilled in the art.

Additionally, in some embodiments, wherein the sensor is configured for implantation into host tissue, the resistance domain is configured to interface with the host tissue and to provide a bioprotective barrier that protects the sensor from cellular invasion. While not wishing to be bound by theory, it is believed that many cellulosic polymers provide sufficient biodurability to protect the host tissue from the underlying membrane system (and vice versa).

Electrode Domain

In some embodiments, the membrane system comprises an optional electrode domain (not shown). The electrode domain is provided to ensure that an electrochemical reaction occurs between the electroactive surfaces of the working electrode and the reference electrode, and thus the electrode domain is preferably situated adjacent to the electroactive surfaces. Preferably, the electrode domain includes a semipermeable coating that maintains a layer of water at the electrochemically reactive surfaces of the sensor, for example, a humectant in a binder material can be employed as an electrode domain; this allows for the full transport of ions in the aqueous environment. The electrode domain can also assist in stabilizing the operation of the sensor by overcoming electrode start-up and drifting problems caused by inadequate electrolyte. The material that forms the electrode domain can also protect against pH-mediated damage that can result from the formation of a large pH gradient due to the electrochemical activity of the electrodes.

In one embodiment, the electrode domain includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain is formed of a curable mixture of a urethane polymer and a hydrophilic polymer. Particularly preferred coatings are formed of a polyurethane polymer having carboxylate functional groups and non-ionic hydrophilic polyether segments, wherein the polyurethane polymer is crosslinked with a water soluble carbodiimide (e.g., 1-ethyl-3-(3-dimethylaminopropyl)carbodiimide (EDC))) in the presence of polyvinylpyrrolidone and cured at a moderate temperature of about 50° C.

Preferably, the electrode domain is deposited by spray or dip-coating the electroactive surfaces of the sensor. More preferably, the electrode domain is formed by dip-coating the electroactive surfaces in an electrode solution and curing the domain for a time of from about 15 to about 30 minutes at a temperature of from about 40 to about 55° C. (and can be accomplished under vacuum (e.g., 20 to 30 in Hg)). In embodiments wherein dip-coating is used to deposit the electrode domain, a preferred insertion rate of from about 1 to about 3 inches per minute, with a preferred dwell time of from about 0.5 to about 2 minutes, and a preferred withdrawal rate of from about 0.25 to about 2 inches per minute provide a functional coating. However, values outside of those set forth above can be acceptable or even desirable in certain embodiments, for example, dependent upon viscosity and surface tension as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments, sufficient hydrophilicity can be provided in the interference domain and/or enzyme domain (e.g., the domain adjacent to the electroactive surfaces) so as to provide for the full transport of ions in the aqueous environment (e.g. without a distinct electrode domain).

Oxygen Conduit

As described above, certain sensors depend upon an enzyme within the membrane system through which the host's bodily fluid passes and in which the analyte (for example, glucose) within the bodily fluid reacts in the presence of a co-reactant (for example, oxygen) to generate a product. The product is then measured using electrochemical methods, and thus the output of an electrode system functions as a measure of the analyte. For example, when the sensor is a glucose oxidase based glucose sensor, the species measured at the working electrode is $H_2O_2$. An enzyme, glucose oxidase, catalyzes the conversion of oxygen and glucose to hydrogen peroxide and gluconate according to the following reaction:

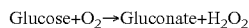

Glucose+$O_2$→Gluconate+$H_2O_2$

Because for each glucose molecule reacted there is a proportional change in the product, $H_2O_2$, one can monitor the change in $H_2O_2$ to determine glucose concentration. Oxidation of $H_2O_2$ by the working electrode is balanced by reduction of ambient oxygen, enzyme generated $H_2O_2$ and other reducible species at a counter electrode, for example. See Fraser, D. M., "An Introduction to In vivo Biosensing: Progress and Problems." In "Biosensors and the Body," D. M. Fraser, ed., 1997, pp. 1-56 John Wiley and Sons, New York))

In vivo, glucose concentration is generally about one hundred times or more that of the oxygen concentration. Consequently, oxygen is a limiting reactant in the electrochemical reaction, and when insufficient oxygen is provided to the sensor, the sensor is unable to accurately measure glucose concentration. Thus, depressed sensor function or inaccuracy is believed to be a result of problems in availability of oxygen to the enzyme and/or electroactive surface(s).

Accordingly, in an alternative embodiment, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

Porous Biointerface Materials

In alternative embodiments, the distal portion 42 includes a porous material disposed over some portion thereof, which modifies the host's tissue response to the sensor. In some embodiments, the porous material surrounding the sensor advantageously enhances and extends sensor performance and lifetime in the short term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, triblock, alternating, random and graft copolymers, as well as metals, ceramics, cellulose, hydrogel polymers, poly(2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), hydroxyethylmethacrylate, hydroxyapeptite, alumina, zirconia, carbon fiber, aluminum, calcium phosphate, titanium, titanium alloy, nintinol, stainless steel, and CoCr alloy, or the like, such as are described in U.S. Publ. No. US-2005-0031689-A1 and U.S. Publ. No. US-2005-0112169-A1.

In some embodiments, the porous material surrounding the sensor provides unique advantages in the short term (e.g., one to 14 days) that can be used to enhance and extend sensor performance and lifetime. However, such materials can also provide advantages in the long term too (e.g., greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion 42 of the sensor. High oxygen solubility materials are materials that dynamically retain a high availability of oxygen that can be used to compensate for the local oxygen deficit during times of transient ischemia (e.g., silicone and fluorocarbons). It is believed that some signal noise normally seen by a conventional sensor can be attributed to an oxygen deficit. In one exemplary embodiment, porous silicone surrounds the sensor and thereby effectively increases the concentration of oxygen local (proximal) to the sensor. Thus, an increase in oxygen availability proximal to the sensor as achieved by this embodiment ensures that an excess of oxygen over glucose is provided to the sensor; thereby reducing the likelihood of oxygen limited reactions therein. Accordingly, by providing a high oxygen solubility material (e.g., porous silicone) surrounding the in vivo portion of the sensor, it is believed that increased oxygen availability, reduced signal noise, longevity, and ultimately enhanced sensor performance can be achieved.

Bioactive Agents

In some alternative embodiments, a bioactive agent is incorporated into the above described porous material and/or membrane system, such as is described in U.S. Publ. No. US-2005-0031689-A1, which diffuses out into the environment adjacent to the sensing region. Additionally or alternately, a bioactive agent can be administered locally at the exit-site or implantation-site. Suitable bioactive agents are those that modify the host's tissue response to the sensor, for example anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, vascularization-inducing compounds, antisense molecules, or mixtures thereof, such as are described in more detail in U.S. Publ. No. US-2005-0031689-A1.

In embodiments wherein the porous material is designed to enhance short-term (e.g., from about 1 to about 14 days) lifetime or performance of the sensor, a suitable bioactive agent can be chosen to ensure that tissue ingrowth does not substantially occur within the pores of the porous material. Namely, by providing a tissue modifying bioactive agent, such as an anti-inflammatory agent (for example, Dexamethasone), substantially tissue ingrowth can be inhibited, at least in the short term, in order to maintain sufficient glucose transport through the pores of the porous material to maintain a stable sensitivity.

In embodiments wherein the porous material is designed to enhance long-term (e.g., from about a day to about a year or more) lifetime or performance of the sensor, a suitable bioactive agent, such as a vascularization-inducing compound or anti-barrier cell compound, can be chosen to encourage tissue ingrowth without barrier cell formation.

Membrane Architectures

Although the illustrated embodiment describes one preferred membrane architecture, namely, an interference domain proximal to the electroactive surfaces, an enzyme domain more distal to the electroactive surfaces than the interference domain, and a resistance domain more distal to the electroactive surfaces than the enzyme domain, a variety of alternative membrane architectures can be utilized. In one alternative embodiment, the enzyme domain is proximal to the electroactive surfaces and the interference domain is more distal to the electroactive surfaces than the enzyme domain. In another alternative embodiment, the enzyme domain is proximal to the electroactive surfaces and the interference domain is more distal to the electroactive surfaces than the enzyme domain as described above, however an electrode domain is located between the enzyme domain and the electroactive surfaces. In another alternative embodiment, an interference domain is more distal to the electroactive surfaces than the resistance domain. In yet another alternative embodiment, an interference domain is more distal to the electrode surface than the enzyme domain. In fact, a variety of alternative membrane configurations are possible within the scope of the preferred embodiments, as is appreciated by one skilled in the art.

In certain embodiments, a variable frequency microwave oven can be used to cure the membrane domains/layers. In general, microwave ovens directly excite the rotational mode of solvents. Consequently, microwave ovens cure coatings from the inside out rather than from the outside in as with conventional convection ovens. This direct rotational mode excitation is responsible for the typically observed "fast" curing within a microwave oven. In contrast to conventional microwave ovens, which rely upon a fixed frequency of emission that can cause arcing of dielectric (metallic) substrates if placed within a conventional microwave oven, Variable Frequency Microwave (VFM) ovens emit thousands of frequencies within 100 milliseconds, which substantially eliminates arcing of dielectric substrates. Consequently, the membrane domains/layers can be cured even after deposition on metallic electrodes as described herein. While not wishing to be bound by theory, it is believe that VFM curing can increase the rate and completeness of solvent evaporation from a liquid membrane solution applied to a sensor, as compared to the rate and completeness of solvent evaporation observed for curing in conventional convection ovens.

In certain embodiments, VFM is can be used together with convection oven curing to further accelerate cure time. In some sensor applications wherein the membrane is cured prior to application on the electrode (see, for example, U.S. Publication No. US-2005-0245799-A1), conventional microwave ovens (e.g., fixed frequency microwave ovens) can be used to cure the membrane layer.

Treatment of Resistance Domain/Membrane System

Although the above-described membrane systems generally include a curing step in formation of the membrane system, including the resistance domain, some alternative embodiments further include an additional treatment step, which may be performed directly after the formation of the resistance domain and/or some time after the formation of the entire membrane system (and anytime in between). In some embodiments, the additional treatment step is performed during (in combination with) sterilization of the sensor.

In some embodiments, the membrane system (or resistance domain) is treated by exposure to ionizing radiation, for example electron beam radiation, UV radiation, X-ray radiation, gamma radiation, and the like. While not wishing to be bound by theory, it is believed that exposing the resistance domain to ionizing radiation substantially cross links the resistance domain and thereby creates a tighter, less permeable network than a resistance domain that has not been exposed to ionizing radiation.

In some embodiments, the membrane system (or resistance domain) is crosslinked by forming free radicals, which may include the use of ionizing radiation, thermal initiators, chemical initiators, photoinitiators (e.g., UV and visible light), and the like. Any suitable initiator or any suitable initiator system can be employed, for example, α-hydroxyketone, α-aminoketone, ammonium persulfate (APS), redox systems such as APS/bisulfite, or potassium permanganate. Suitable thermal initiators include but are not limited to potassium persulfate, ammonium persulfate, sodium persulfate, and mixtures thereof.

While not wishing to be bound by theory, it is believed that cross linking the resistance domain to form free radicals effectively forms covalent bonds that create a tighter, less permeable network than a resistance domain that has not been cross linked.

In embodiments wherein electron beam radiation is used to treat the membrane system (or resistance domain), a preferred exposure time is from about 6 Kilo-Gray (kGy) or about 12 kGy to about 25 kGy or about 50 kGy, and more preferably 25 kGy. However, one skilled in the art can appreciate that choice of molecular weight, composition of cellulosic polymer (or other polymer) and/or thickness of layer can affect the preferred exposure time of membrane to radiation. Preferably, the exposure is sufficient for substantially cross linking the resistance domain to form free radicals, but does not destroy or break down the membrane or does not damage the underlying electroactive surfaces.

In embodiments wherein UV radiation is employed to treat the membrane, UV rays from about 200 nm to about 400 nm are preferred; however values outside of this range are possible dependent upon the cellulosic polymer and/or other polymer used.

In general, sterilization of the transcutaneous sensor can be completed after final assembly, utilizing methods such as electron beam radiation, gamma radiation, glutaraldehyde treatment, or the like. The sensor can be sterilized prior to or after packaging. In an alternative embodiment, one or more sensors can be sterilized using variable frequency microwave chamber(s), which can increase the speed and reduce the cost of the sterilization process. In another alternative embodiment, one or more sensors can be sterilized using ethylene oxide (EtO) gas sterilization, for example, by treating with 100% ethylene oxide, which can be used when the sensor electronics are not detachably connected to the sensor and/or when the sensor electronics must undergo a sterilization process. In one embodiment, one or more packaged sets of transcutaneous sensors (e.g., 1, 2, 3, 4, or 5 sensors or more) are sterilized simultaneously.

Experiments

The following examples serve to illustrate certain preferred embodiments and aspects and are not to be construed as limiting the scope thereof.

Transcutaneous Glucose Sensor with Cellulose Acetate Resistance Domain

A short term (transcutaneous) sensor was generally built by providing a platinum wire, vapor-depositing the platinum with Parylene to form an insulating coating, helically winding a silver wire around the insulated platinum wire (to form a "twisted pair"), masking sections of electroactive surface of the silver wire, vapor-depositing Parylene on the twisted pair, chloridizing the silver electrode to form silver chloride reference electrode, and removing a radial window on the insulated platinum wire to expose a circumferential electroactive working electrode surface area thereon, this assembly also referred to as a "parylene-coated twisted pair assembly" (which is described in more detail in U.S. Publ. No. US-2006-0020187-A1).

An interference domain was formed on the parylene-coated twisted pair assembly by dip coating in an interference domain solution comprising 7 weight percent, 50,000 molecular weight cellulose acetate (Aldrich 419028 St. Louis, Mo.) in a 2:1 acetone/ethanol solvent solution, followed by drying at room temperature for 3 minutes. This interference domain solution dip coating step was repeated three more times to form an interference domain comprised of four layers of cellulose acetate on the assembly. The dip length (insertion depth) was adjusted to ensure that the cellulose acetate covered from the tip of the working electrode, over the exposed electroactive working electrode window, to cover a distal portion of the exposed electroactive reference electrode.

An enzyme domain was formed over the interference domain by subsequently dip coating the assembly in an enzyme domain solution and drying in a vacuum oven for 20 minutes at 50° C. This dip coating process was repeated once more to form an enzyme domain comprised of two layers.

A resistance domain was formed over the enzyme domain using a resistance domain solution comprising 7 weight percent, 38,000 molecular weight cellulose acetate (Eastman CA-320S, Kingsport, Tenn.) in a 90:10 acetone/water solvent solution, followed by drying at room temperature for 3 minutes. The cellulose acetate used in this test included an acetyl content of about 32.0 wt % and a hydroxyl content of about 8.7 wt %. This resistance domain solution dip coating step was repeated two more times to form a resistance domain comprised of three layers of cellulose acetate on the assembly.

In vitro tests were run to evaluate the ability of the sensor to pass glucose and oxygen. Namely, the sensor was immersed in 40, 200, and 400 mg/dL glucose solutions, and subsequently in 6, 0.6, and 0.25 mg/L oxygen solutions while immersed in 400 mg/dL glucose, while its electrical signal was monitored. The results are shown in FIGS. 3A to 3B.

Figure 3A:
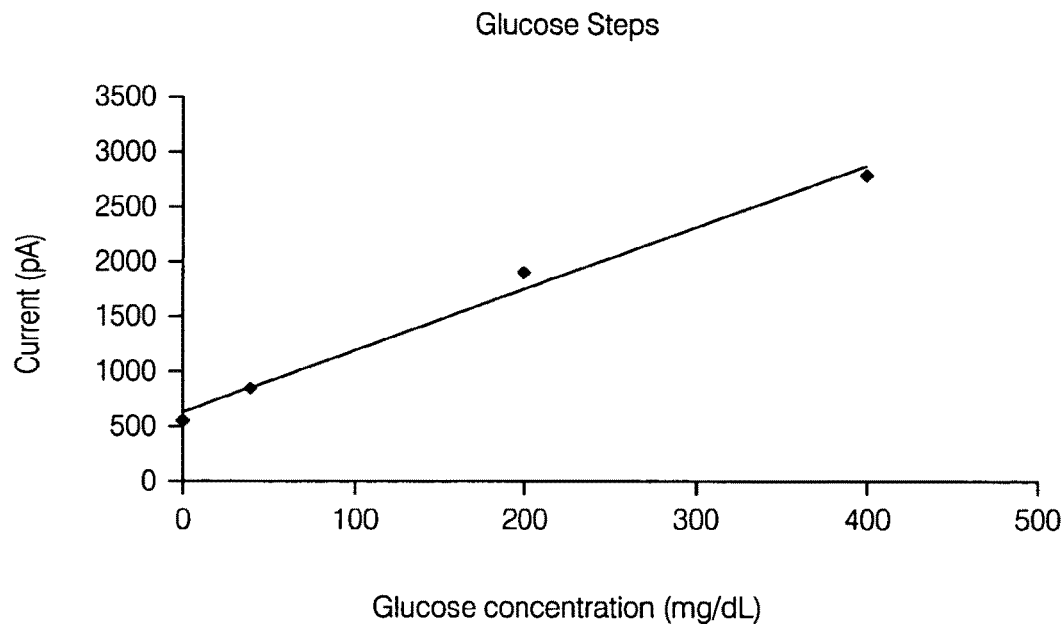
FIG. 3A is a graphical representation that illustrates a sensor's response to glucose in one experiment.

FIG. 3A is a graph that illustrates sensor's response to each glucose solution (40, 200, and 400 mg/dL glucose steps). The x-axis represents glucose in mg/dL; the y-axis represents current in picoAmps. Namely, the sensor's response is plotted for each glucose step and the data points regressed to determine the slope (and intercept) of the sensor. The resulting slope is about 5.5 with an $R^2$ value of about 0.9882 showing that the sensor performs well and has a functional slope and excellent linearity.

Figure 3B:
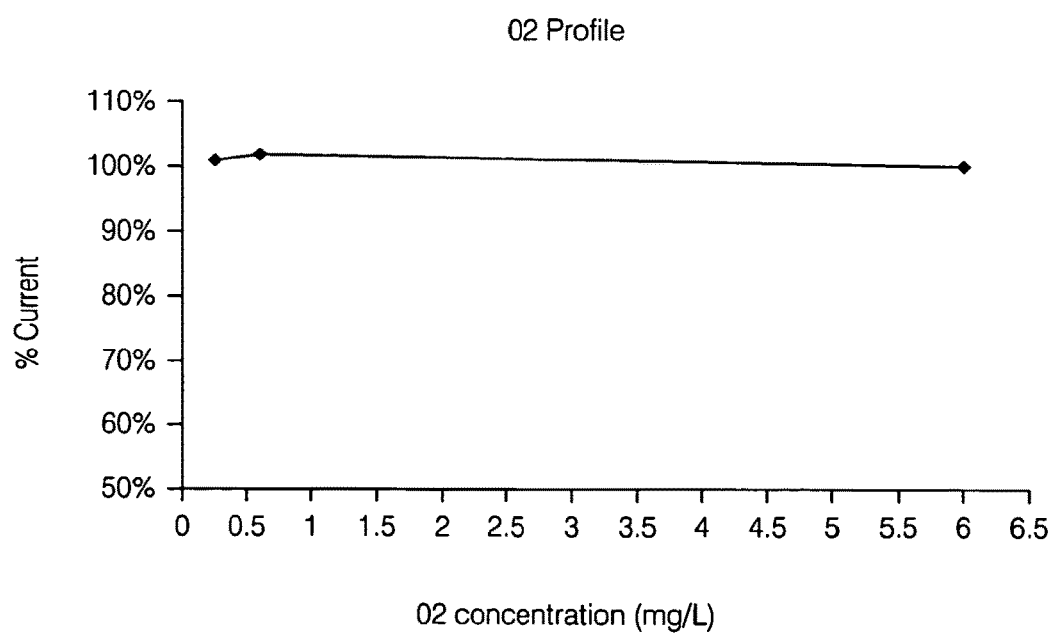
FIG. 3B is a graphical representation that illustrates a sensor's response to oxygen in one experiment.

FIG. 3B is a graph that illustrates sensor's response to each oxygen solution (6, 0.6, and 0.25 mg/L oxygen steps). The x-axis represents oxygen in mg/L; the y-axis represents current as a percentage of signal at 6 mg/L oxygen when a glucose concentration of 400 mg/dL is present. Namely, the sensor's response is plotted for each oxygen step and shows approximately 100% oxygen performance. Accordingly, it is believed that a glucose sensor built with a cellulose acetate resistance domain as described herein is capable of controlling the flux of glucose and oxygen through the resistance domain such that glucose can be accurately measured within clinically relevant ranges (e.g., about 40 to about 400 mg/dL).

Subsequently, the above-described sensor was exposed to 25 kGy electron beam radiation, and the sensor was again immersed in 40, 200 and 400 mg/dL glucose solutions, and subsequently in 6, 0.6, and 0.25 mg/L oxygen solutions while in 400 mg/dL glucose, while its electrical signal was monitored. The results are shown in FIGS. 4A to 4B.

Figure 4A:
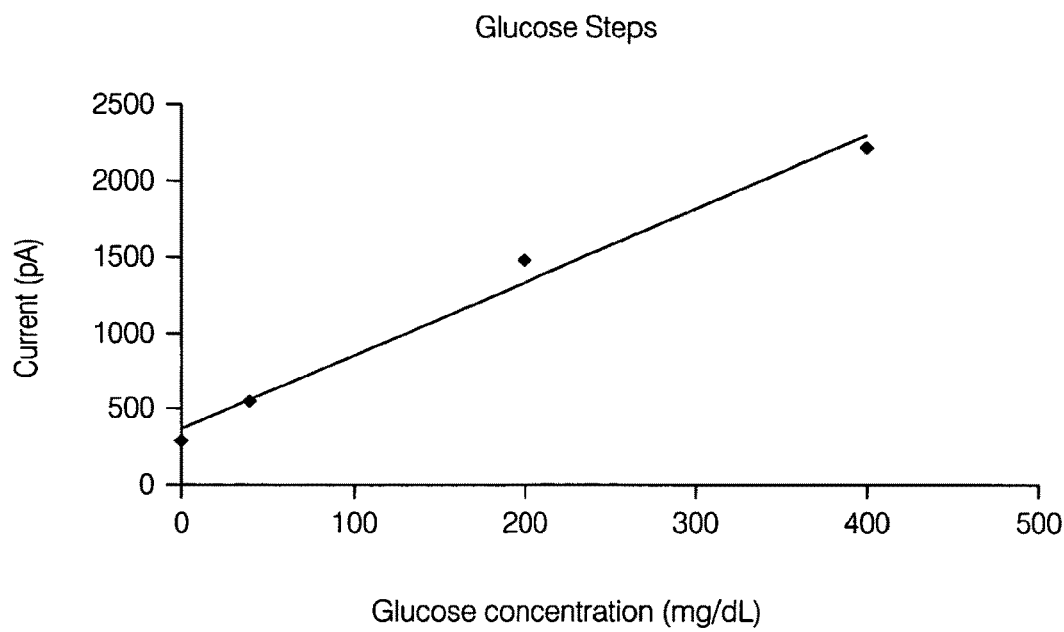
FIG. 4A is a graphical representation that illustrates a sensor's response to glucose in another experiment.

FIG. 4A is a graph that illustrates sensor's response to each glucose solution (40, 200, and 400 mg/dL glucose steps). The x-axis represents glucose in mg/dL; the y-axis represents current in picoAmps. Namely, the sensor's response is plotted for each glucose step and the data points regressed to determine the slope (and intercept) of the sensor. The resulting slope is about 4.8 with an $R^2$ value of about 0.9849 showing that the sensor performance is substantially sustained after electron beam exposure. While not wishing to be bound by theory, it is believed that the slight decrease in slope after electron beam irradiation may be caused by cross linking of the cellulose acetate, which is believed to form a tighter, less permeable network.

Figure 4B:
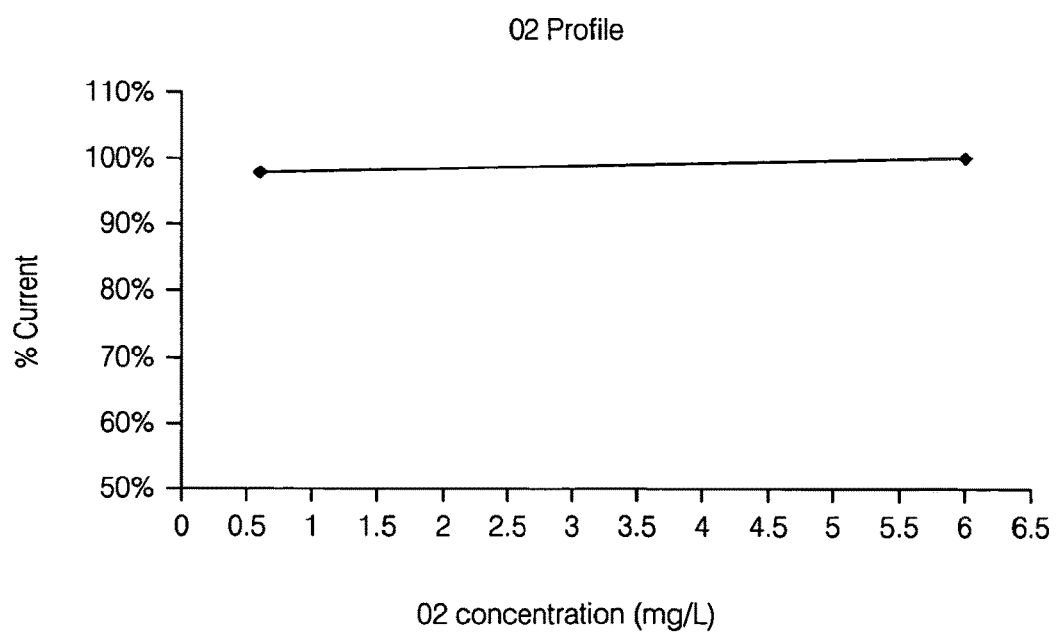
FIG. 4B is a graphical representation that illustrates a sensor's response to oxygen in another experiment.

FIG. 4B is a graph that illustrates sensor's response to each oxygen solution (6 and 0.6 mg/L oxygen steps). The x-axis represents oxygen in mg/L; the y-axis represents current as a percentage of signal at 6 mg/L oxygen when a glucose concentration of 400 mg/dL is present. Namely, the sensor's response is plotted for each oxygen step and shows approximately 100% oxygen performance down to 0.6 mg/L.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for forming a transcutaneous analyte sensor for measuring an analyte in a host, the method comprising:
   forming a membrane system on an electroactive surface of the transcutaneous analyte sensor, wherein the transcutaneous analyte sensor comprises an in vivo portion and an ex vivo portion, wherein the in vivo portion is configured to be exposed to interstitial fluid, wherein the membrane system comprises a resistance domain configured to control a flux of the analyte therethrough and an enzyme configured to catalyze a reaction of the analyte and oxygen from the interstitial fluid surrounding the membrane system, wherein the resistance domain is formed to comprise a hydrophilic portion and a hydrophobic portion, wherein the resistance domain is formed with an oxygen to glucose permeability ratio of less than about 400:1, and wherein the membrane system is formed of a material that provides substantially constant signal output when the transcutaneous analyte sensor is at an analyte concentration of 400 mg/dL glucose while oxygen concentration is dropped from 0.6 mg/L to 0.25 mg/L;
   forming an oxygen conduit portion extending from the ex vivo portion of the transcutaneous analyte sensor to the in vivo portion of the transcutaneous analyte sensor;
   crosslinking at least a portion of the membrane system;
   conducting a test of the transcutaneous analyte sensor to confirm that the transcutaneous analyte sensor demonstrates substantial linearity up to an analyte concentration of at least 400 mg/dL, wherein substantial linearity is associated with a R2 correlation that meets a predetermined criteria;
   conducting a test of the transcutaneous analyte sensor by monitoring for a substantially constant signal output from the transcutaneous analyte sensor as an oxygen concentration level surrounding the sensor is decreased to a predetermined level;
   measuring a sensitivity of the sensor;
   determining that the sensitivity is a functional sensitivity;
   inserting the transcutaneous analyte sensor into a package, whereby the package holds a plurality of transcutaneous analyte sensors; and
   sterilizing the plurality of transcutaneous analyte sensors in the package simultaneously.

2. The method of claim 1, wherein the membrane system is formed on the electroactive surface using a deposition technique selected from the group consisting of dip coating, spray coating, spin coating, and casting.

3. The method of claim 2, wherein the resistance domain is formed by dip coating.

4. The method of claim 2, further comprising the step of curing the resistance domain for at least about 2 minutes at ambient temperature.

5. The method of claim 2, wherein the resistance domain is formed by dip coating an insertion rate of about 40 inches per minute.

6. The method of claim 2, wherein the resistance domain is formed by dip coating at a dwell time of less than about 1 second.

7. The method of claim 2, wherein the resistance domain is formed by dip coating at a withdrawal rate of about 40 inches per minute.

8. The method of claim 1, wherein the membrane system further comprises an enzyme domain comprising a co-reactant, wherein the co-reactant is capable of undergoing a reaction with the analyte, and wherein the enzyme domain is formed prior to formation of the resistance domain.

9. The method of claim 1, wherein the material comprises a hydrophilic-hydrophobic macromolecule comprising a cellulosic polymer.

10. The method of claim 9, wherein the cellulosic polymer comprises cellulose acetate.

11. The method of claim 9, wherein the cellulosic polymer comprises from about 3 wt. % to about 10 wt. % cellulose acetate.

12. The method of claim 9, wherein the cellulosic polymer comprises about 7 wt. % cellulose acetate.

13. The method of claim 1, wherein conducting the test of the transcutaneous analyte sensor includes monitoring for a substantially constant signal output from the transcutaneous analyte sensor as the oxygen concentration level surrounding the sensor is decreased to 0.25 mg/L.

14. The method of claim 1, wherein conducting the test of the transcutaneous analyte sensor includes monitoring for a substantially constant signal output from the transcutaneous analyte sensor as an oxygen concentration level surrounding the sensor is decreased from 0.6 mg/L to 0.25 mg/L.

* * * * *

UNITED STATES PATENT AND TRADEMARK OFFICE
CERTIFICATE OF CORRECTION

PATENT NO. : 10,300,507 B2
APPLICATION NO. : 14/181434
DATED : May 28, 2019
INVENTOR(S) : James R. Petisce Page 1 of 2

It is certified that error appears in the above-identified patent and that said Letters Patent is hereby corrected as shown below:

On the Title Page

Item (56) Page 8 Column 1 at Line 62, Under Other Publications, change "series" to --series analysis--.

Item (56) Page 8 Column 2 at Line 10, Under Other Publications, change "sensor." to --sensor. J.--.

Item (56) Page 9 Column 1 at Line 64, Under Other Publications, change "Heiler," to --Heller,--.

Item (56) Page 9 Column 1 at Line 67, Under Other Publications, change "Heiler," to --Heller,--.

Item (56) Page 10 Column 1 at Line 38, Under Other Publications, change "giucose" to --glucose--.

Item (56) Page 10 Column 1 at Line 54, Under Other Publications, change "base" to --based--.

Item (56) Page 10 Column 2 at Line 15, Under Other Publications, change "-Aminopropyitriethoxysilane" to -- -Aminopropyltriethoxysilane--.

Item (56) Page 10 Column 2 at Line 18, Under Other Publications, change "Pregress" to --Progress--.

Item (56) Page 10 Column 2 at Line 24, Under Other Publications, change "Analytics" to --Analytica--.

Item (56) Page 11 Column 2 at Line 34, Under Other Publications, change "Pecoraro" to --Pegoraro--.

Item (56) Page 13 Column 1 at Line 48, Under Other Publications, change "Analytics" to --Analytica--.

Item (56) Page 15 Column 1 at Line 5, Under Other Publications, change "Jun." to --July.--.

Signed and Sealed this
Seventeenth Day of September, 2019

Andrei Iancu
*Director of the United States Patent and Trademark Office*

CERTIFICATE OF CORRECTION (continued)
U.S. Pat. No. 10,300,507 B2

In the Specification

In Column 2 at Line 62, Change "carboxyethyl" to --carboxyethyl.--.

In Column 7 at Line 35, Change "thereon" to --thereon.--.

In Column 8 at Lines 9-10, Change "/tyro sine," to --/tyrosine,--.

In Column 8 at Line 10, Change "andrenostenedione;" to --androstenedione;--.

In Column 8 at Line 12, Change "biotimidase;" to --biotinidase;--.

In Column 8 at Line 26, Change "diptheria/" to --diphtheria/--.

In Column 8 at Line 33, Change "perioxidase;" to --peroxidase;--.

In Column 8 at Line 39, Change "phenyloin;" to --phenytoin;--.

In Column 8 at Line 42, Change "sissomicin;" to --sisomicin;--.

In Column 8 at Line 46, Change "duodenalisa," to --duodenalis,--.

In Column 8 at Line 54, Change "Trepenoma pallidium," to --Treponema pallidum,--.

In Column 8 at Line 55, Change "stomatis" to --stomatitis--.

In Column 9 at Lines 8-9 (Approx.), Change "(barbituates," to --(barbiturates,--.

In Column 9 at Line 37, Change "and or" to --and/or--.

In Column 10 at Lines 51-52, Change "tetrafluorethylene" to --tetrafluoroethylene--.

In Column 25 at Line 11, Change "(EDC)))" to --(EDC))--.

In Column 25 at Line 64, Change "York))" to --York)).--.

In Column 26 at Line 45, Change "poly(l-lysine)," to --poly(l-lysine),--.

In Column 26 at Line 46, Change "hydroxyapeptite," to --hydroxyapatite,--.

In Column 26 at Line 48, Change "nintinol," to --nitinol,--.